United States Patent
Jain et al.

(10) Patent No.: US 10,521,557 B2
(45) Date of Patent: Dec. 31, 2019

(54) SYSTEMS AND METHODS FOR PROVIDING DYNAMIC, INDIVIDUALIZED DIGITAL THERAPEUTICS FOR CANCER PREVENTION, DETECTION, TREATMENT, AND SURVIVORSHIP

(71) Applicant: Vignet Incorporated, Fairfax, VA (US)

(72) Inventors: Praduman Jain, Fairfax, VA (US); Dave Klein, Oakton, VA (US); Neeta Jain, Fairfax, VA (US); Yue Cao, Vienna, VA (US)

(73) Assignee: Vignet Incorporated, Farifax, VA (US)

( * ) Notice: Subject to any disclaimer, the term of this patent is extended or adjusted under 35 U.S.C. 154(b) by 0 days.

(21) Appl. No.: 15/803,556

(22) Filed: Nov. 3, 2017

(65) Prior Publication Data
US 2019/0243944 A1    Aug. 8, 2019

(51) Int. Cl.
| | | |
|---|---|---|
| *G16H 80/00* | (2018.01) | |
| *G06F 19/00* | (2018.01) | |
| *G16H 50/30* | (2018.01) | |
| *G16H 10/60* | (2018.01) | |
| *G06F 16/9535* | (2019.01) | |
| *G06N 5/02* | (2006.01) | |
| *G16H 40/63* | (2018.01) | |
| *G06N 20/00* | (2019.01) | |

(52) U.S. Cl.
CPC ........ *G06F 19/326* (2013.01); *G06F 16/9535* (2019.01); *G06F 19/3418* (2013.01); *G16H 10/60* (2018.01); *G16H 50/30* (2018.01); *G06N 5/027* (2013.01); *G06N 20/00* (2019.01); *G16H 40/63* (2018.01)

(58) Field of Classification Search
CPC ....... G16H 10/60; G16H 80/00; G06F 19/326
See application file for complete search history.

(56) References Cited

U.S. PATENT DOCUMENTS

| | | | |
|---|---|---|---|
| 6,039,688 | A | 3/2000 | Douglas et al. |
| 6,260,022 | B1 | 7/2001 | Brown |
| 6,269,339 | B1 | 7/2001 | Silver |
| 7,076,534 | B1 | 7/2006 | Cleron et al. |
| 7,330,717 | B2 | 2/2008 | Gidron et al. |
| 7,447,643 | B1 | 11/2008 | Olson et al. |
| 7,730,063 | B2 | 6/2010 | Eder |

(Continued)

FOREIGN PATENT DOCUMENTS

| | | |
|---|---|---|
| EP | 2 545 468 | 3/1951 |
| WO | WO 2011/112556 | 9/2011 |

(Continued)

OTHER PUBLICATIONS

"Cancer Care Patient Navigation. A practical guide for community cancer centers," Association of Community Cancer Centers, 2009, [retrieved on Jan. 2, 2018], retrieved from: URL <https://www.accc-cancer.org/resources/pdf/Patient-Navigation-Guide.pdf>, 40 pages.

(Continued)

*Primary Examiner* — John A Pauls
(74) *Attorney, Agent, or Firm* — Fish & Richardson P.C.

(57) ABSTRACT

Methods, systems, and apparatus, including computer programs stored on a computer-readable storage medium, for providing dynamic, individualized digital therapeutics for cancer patients and cancer survivors.

19 Claims, 11 Drawing Sheets

(56) References Cited

U.S. PATENT DOCUMENTS

| | | |
|---|---|---|
| 9,361,011 B1 | 6/2016 | Burns |
| 9,426,433 B1 | 8/2016 | Mazzarella |
| 9,461,972 B1 | 10/2016 | Mehta |
| 2001/0019338 A1 | 9/2001 | Roth |
| 2002/0010596 A1* | 1/2002 | Matory ................ A61B 5/0002 705/2 |
| 2002/0022973 A1 | 2/2002 | Sun |
| 2003/0165954 A1 | 9/2003 | Katagiri et al. |
| 2003/0182429 A1* | 9/2003 | Jagels ............... H04L 29/06027 709/227 |
| 2004/0030424 A1* | 2/2004 | Corl, Jr. ............. H04L 63/0236 700/90 |
| 2004/0203755 A1 | 10/2004 | Brunet et al. |
| 2005/0086587 A1 | 4/2005 | Balz |
| 2005/0186550 A1 | 8/2005 | Gillani |
| 2005/0246304 A1 | 11/2005 | Knight et al. |
| 2006/0041452 A1 | 2/2006 | Kukarni |
| 2006/0107219 A1 | 5/2006 | Ahya |
| 2006/0205564 A1 | 9/2006 | Peterson |
| 2007/0021984 A1 | 1/2007 | Brown |
| 2007/0172844 A1 | 7/2007 | Lancaster et al. |
| 2007/0231828 A1 | 10/2007 | Beachy et al. |
| 2007/0259351 A1 | 11/2007 | Chinitz et al. |
| 2007/0281285 A1 | 12/2007 | Jayaweera |
| 2008/0005679 A1 | 1/2008 | Rimas-Ribikauskas |
| 2008/0127040 A1 | 5/2008 | Barcellona |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0311968 A1 | 12/2008 | Hunter |
| 2009/0023555 A1 | 1/2009 | Raymond |
| 2009/0024944 A1 | 1/2009 | Louch |
| 2009/0031215 A1* | 1/2009 | Collier, II ............. G06F 17/211 715/255 |
| 2009/0035733 A1* | 2/2009 | Meitar ..................... G09B 7/00 434/118 |
| 2009/0043689 A1 | 2/2009 | Yang |
| 2009/0076856 A1 | 3/2009 | Darby et al. |
| 2009/0125333 A1* | 5/2009 | Heywood ............ A61B 5/0002 705/3 |
| 2009/0163182 A1 | 6/2009 | Gatti |
| 2009/0170715 A1 | 7/2009 | Glinsky |
| 2009/0172002 A1 | 7/2009 | Bathiche |
| 2010/0041378 A1 | 2/2010 | Aceves |
| 2010/0082367 A1 | 4/2010 | Hains et al. |
| 2010/0179833 A1 | 7/2010 | Roizen et al. |
| 2010/0211941 A1 | 8/2010 | Roseborough |
| 2010/0250341 A1 | 9/2010 | Hauser |
| 2011/0184748 A1 | 7/2011 | Fierro et al. |
| 2011/0200979 A1 | 8/2011 | Benson |
| 2011/0230360 A1 | 9/2011 | Stephan et al. |
| 2012/0102050 A1 | 4/2012 | Button |
| 2012/0272156 A1 | 10/2012 | Kerger |
| 2013/0110565 A1 | 5/2013 | Means |
| 2013/0166494 A1 | 6/2013 | Davis |
| 2013/0238686 A1 | 9/2013 | O'Donoghue |
| 2014/0019191 A1* | 1/2014 | Mulji ............... G06Q 10/06316 705/7.26 |
| 2014/0088995 A1 | 3/2014 | Damani |
| 2014/0100883 A1 | 4/2014 | Hamilton |
| 2014/0156823 A1 | 6/2014 | Liu |
| 2014/0181715 A1 | 6/2014 | Axelrod |
| 2014/0240122 A1 | 8/2014 | Roberts |
| 2014/0273913 A1 | 9/2014 | Michel |
| 2015/0019342 A1 | 1/2015 | Gupta |
| 2015/0025997 A1 | 1/2015 | Tilenius et al. |
| 2015/0056589 A1 | 2/2015 | Zhang et al. |
| 2015/0135160 A1 | 5/2015 | Gauvin |
| 2015/0148061 A1 | 5/2015 | Koukoumidis |
| 2015/0356701 A1* | 12/2015 | Gandy ................... G06Q 50/22 705/2 |
| 2016/0058287 A1 | 3/2016 | Dyell |
| 2016/0189317 A1* | 6/2016 | Papandrea ............ G06F 19/326 705/319 |
| 2017/0132395 A1 | 5/2017 | Futch |

FOREIGN PATENT DOCUMENTS

| | | |
|---|---|---|
| WO | WO 2016/161416 | 10/2016 |
| WO | WO 2017/106770 | 6/2017 |

OTHER PUBLICATIONS

[No Author Listed] "Digital therapeutics," Wikipedia, Nov. 20, 2017, [retrieved on Jan. 2, 2018], retrieved from: URL <https://en.wikipedia.org/wiki/Digital_therapeutics>, 4 pages.

[No Author] "Methods for JITAIs Just in Time Adaptive Intervention," 2016, Nov. 9, 2016, [retrieved on Nov. 9, 2016], from the internet <https://community.isr.umich.edu/public/Default.aspx?alias=community.isr.umich.edu/public/jitai&>, 1 pages.

Braun et al., "Cancer Patient Navigator Tasks across the Cancer Care Continuum," J Health Care Poor Underserved, Feb. 1, 2012, 23(1):398-413.

Conner, "Experience sampling and ecological momentary assessment with mobile phones," 2015—http://www.otago.ac.nz/psychology/otago047475.pdf, 4 pages.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

Heron, "Ecological Momentary Intervention [EMI]: Incorporating mobile technology into a disordered eating treatment program for college women," Psychology—Dissertations, paper 157, 2011.

http://www.khanacademic.org, 2017, 1 page.

Milward, "Ecological momentary assessment," Jul. 2015, [retrieved on May 12, 2017], from the internet <https://www.addiction-ssa.org/commentary/emerging-research-methods-series-ecological-momentary-assessment>, 3 pages.

Runyan et al., "Virtues, ecological momentary assessment/intervention and smartphone technology," Front Psychol, 2015;6:481, 24 pages.

Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.

Simon, "Patient Navigators Help Cancer Patients Manage Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.

Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.

* cited by examiner

150c

‹ Weekly Challenges

Sign-up now

- [ ] Eat out less than 3 times
- [ ] Ask for help
- [x] Get some daylight

Coming up next:

- Practice smart food shopping habits
- Practice Awareness
- Get some exercise

Post Challenges accepted:

- Get 10,000 steps a day ★
- Yoga
- Meditation ★
- Examine your expectations

FIG. 1D

| Need Help | Patient Name | Days in Program | At Risk For: | Program id |
|---|---|---|---|---|
| ☐ | Patty Smith | 1 | Anxiety, Depression, Fatigue | 126495V |
| ☐ | Rudolf G. | 60 | Anxiety | 0336410 |
| ☐ | Denny R. | 3 | Depression, Fatigue | |
| ☐ | Denny R. | 12 | Depression, Fatigue | |
| ☐ | Denny R. | 20 | Depression | |
| ☐ | Denny R. | 45 | Sexuality, Anxiety | |
| ☐ | Denny R. | 78 | Depression | |
| ☐ | Denny R. | 28 | Depression | |
| ☐ | Denny R. | 89 | Depression | |

SYSTEMS AND METHODS FOR PROVIDING DYNAMIC, INDIVIDUALIZED DIGITAL THERAPEUTICS FOR CANCER PREVENTION, DETECTION, TREATMENT, AND SURVIVORSHIP

TECHNICAL FIELD

This document generally relates to computing techniques that can be used to efficiently provide digital therapeutics and precision medicine.

BACKGROUND

Due to the effectiveness of modern cancer treatment, patients are surviving cancer at higher rates and with longer expected lifespans. However, even after cancer is in remission, many survivors find that their bodies and lifestyles have changed significantly. In many instances, cancer patients and cancer are not provided the support needed to meet their unique individual needs.

SUMMARY

In some implementations, a networked system of devices creates and manages dynamic, individualized care plans for cancer patients and cancer survivors. The system can coordinate digital therapeutics programs across many different aspects of users' wellbeing, taking into consideration interactions, risks, and personalized behavior that would not be apparent to a physician. This allows the system to interact with various other systems to automatically adjust the content of each user's care plan. The system also carries out the plans by administering real-time digital therapeutics that are provided through user devices. The system can react to each user's current situation with contextually relevant interventions. The interactions of the system are not limited to a user whose health and wellness the system supports. Rather, the system can interact with devices of other users, such as friends, family members, medical service providers, and others to support a user's health. The system can also assess unique risk levels for each patient and predictively act to mitigate those risks. Further, the system can use machine learning techniques to identify the combinations of interventions that best improve outcomes for different categories of patients.

One of the advantages of the system is the ability to use a common set of digital therapeutics programs to provide unique, adaptive, personalized interventions for a wide variety of users. The system may also provide real-time or near-real-time responsiveness to adjust the interventions for a user's current status and situation.

In general, maintaining and updating sophisticated software can be difficult, especially as computer systems and requirements change over time. A particular challenge is managing the dependency among different elements of a system. Traditional systems often require static dependency among software components or impose other constraints on relationships between modules, and changes to one component often require updates to many other related components to accommodate the changes. Some systems may use independent components, but these may provide a lower quality results overall, since the components may not effectively share information to provide the best experience to users. Also, sharing information among different software components often incurs significant overhead, in the form of delays and computing resource consumption due to APIs, messaging protocols, network delays, and other factors.

The present application describes solutions to the traditional technical challenges of dependency among sophisticated software systems. In some implementations, the system uses a collection of modules or programs hosted by a server system. The programs can operate in parallel and asynchronously to each other, and can share the same data sets about a user to reduce storage requirements and overhead. As discussed further below, each program may be capable of operating at any of multiple different states, where each program state corresponds to different behavior of the program, e.g., using different sets of rules and interactive content. The set of programs can collectively support many different users, with the system using a user-specific set of program states for each user. For example, if a system had three programs, each with states 1-10, a first user may be supported with the programs at states 1, 3, and 2, a second user may be supported by the same programs operating at states 2, 3, and 5, and so on. The programs can also use common data sets for each user, which are available to all programs, to minimize storage requirements and latency.

The programs can be designed to operate in any of the given programs states independently of the other programs, so that operation or delay of any program does not block operation of other programs in operation. Nevertheless, the system enables interdependence among the programs in the manner that the program states are set. For example, the system can dynamically set the program states of programs for a user according to the program states of other programs for the same user. For example, although each program can represent a self-contained unit that can operate and interact with users separate from other programs, the system may also take into account a user's user-specific program states for all programs when the system evaluates whether to dynamically change program states. Based on the state of one program, the system may determine to change the state of other programs, to achieve an appropriate combination of programs active at any given time for a particular patient. The changes in program state can be made periodically and asynchronously, so that other programs can continue in their current states or change states as needed.

In addition, by re-using the same programs and discrete states of those programs for many users, the system can provide many different combinations of experiences with a small number of programs and states. This maximizes the ability of the system to customize interaction and adapt for individual users, while minimizing storage requirements and effort to maintain the system. For example, a system that uses ten programs with ten states each has a total of 100 individual program states, but provides $10^{10}$ or 10 billion different combinations of program states, where each combination can provide a different user experience. This allows a very large level of flexibility and customizability with high efficiency, e.g., small storage space and minimal computation for the scope of variability allowed. Further, for each combination of program states, the operations of the programs further customizes interaction with the user according to the user's current context, behavior, medical history, history of interactions with the program, and other user data.

Systems that implement these techniques can be very effective at addressing complex scenarios where users experience diverse and changing needs over time. For example, due to the effectiveness of modern cancer treatment, patients are surviving cancer at higher rates and with longer expected lifespans. However, even after cancer is in remission, many survivors find that their bodies and lifestyles have changed significantly. In some instances cancer survivors are given survivorship care plans to help address the challenges of life after cancer treatment. Care plans can also be used for patients undergoing cancer treatment. These care plans are often not tailored to the specific needs of individual patients, and do not reflect patients changing needs over time. Further, once cancer is declared to be in remission, many cancer survivors find themselves without the support that they previously relied on.

In general, cancer prevention, diagnosis, treatment, and survivorship pose unique challenges. One is that cancer and the treatments used generally have systemic effects rather than primarily localized effects on the body. Many times, symptoms during treatment and even in remission come in clusters that are seemingly unrelated to the portions of the body where the cancer is located. For example, after treatment for breast cancer, patients may experience a wide range of symptoms across many aspects of their lifestyle, including changes to sleep patterns, eating habits, activity levels, anxiety levels, pain levels for various different locations of the body, and so on. In many cases, chemotherapy and other treatment may add complications such as neuropathy that the patient may deal with for the rest of their life. The symptoms experienced are highly variable from one patient to the next, and many times cannot be accurately predicted. In addition, the time of onset of the symptoms and the intensity of the symptoms varies greatly as well. As a result, typical care plans for cancer patients and cancer survivors are often inadequate to address the individualized and varying needs of specific patients.

These characteristics of cancer treatment and survivorship are significantly different than other medical conditions, even other chronic conditions. In many types of surgeries, recovery generally proceeds on a predictable timeline with well-characterized results. For example, a knee replacement procedure may have a typical recuperation period of a few months, with a well-known set of outcomes that are likely. Complications are typically predictable and mostly localized to the area of surgery. By contrast, a patient that has undergone chemotherapy for breast cancer may experience diminished sensation or pain in the extremities, e.g., peripheral neuropathy, due to the medications administered. The symptoms affect a person's quality of life in varying ways long after treatment has completed.

Also unlike many medical conditions, the causes and effects of cancer and symptoms are often not well understood. While other conditions like diabetes are ongoing chronic conditions, the nature of the bodily systems affected and the effects on a person's wellbeing are often predictable and well understood. With cancer, however, there are a wide variety of factors. Most cancers by many different risk factors including genetic factors, reactions to medications, lifestyle, environment, and so on. Similarly, the actions that improve wellbeing or relieve symptoms, are also often counterintuitive. For example, pain or anxiety may be helped in some cases by walking, because walking may indirectly stimulate the immune system, change the environment of the patient, and affect other factors that eventually relieve the symptoms.

Another unique aspect of assisting cancer patients and survivors is the sudden decrease in support once cancer is determined to be in remission. During treatment, a cancer patient is usually subject to close monitoring and frequent guidance from medical professionals and others. But once in remission, support and monitoring often end abruptly. This can leave cancer survivors with great uncertainty, and without resources needed to manage risks and lifestyle changes and ongoing symptoms that may result in a quality of life that is very different from before cancer diagnosis.

The systems described in this document can create dynamic care plans using techniques highly suited to the complex needs of cancer patients and survivors. The system provides tools and templates that can be used to create an initial care plan as a combination of various different digital therapeutics programs. From this initial state, the systems dynamically and automatically vary the nature of the care plan according to analysis of the patient's status and history. The system is able to leverage input from a variety of data sources, reflecting the patient's medical history, historical behavior, current physical state, environment, mood, symptoms, medication, and more. This allows the system to provide information, experiences, interventions, and other content that is contextually relevant and adapted to each individual user's needs.

In some implementations, the system includes multiple digital therapeutics programs that each relate to a different aspect of the user's needs. For example, different programs can address different aspects of physical, psychological, emotional, social, and other needs. Each program can have a corresponding set of rules that specify system actions to be performed when appropriate triggers and conditions are satisfied. The system can also use the output of these programs and the state of the programs to adjust the nature of the patient's care plan. For example, the analysis and results of a program addressing anxiety can be used to set the manner in which programs are administered for supporting physical activity, sleep, social engagement, and other aspects of a person's total wellbeing. In this matter, the various programs can be interdependent, with different programs having states that are modified by the system based at least in part on the state of other programs. In this manner, programs that are not directly related in topic or function to other programs can nevertheless affect each other's state. The manner in which these programs interact (e.g., how programs and conditions trigger adjustments in other programs) can be learned by the system through machine learning techniques. With these and other techniques discussed below, the system can monitor health risks and assess needs in a personalized manner and provide digital therapeutics tailored specifically for each individual.

In some implementations, a method includes communicating, by a server system, individualized application content over a network to (i) a first device associated with first user that is a cancer patient or cancer survivor, (ii) a second device associated with a caregiver of the first user, and (iii) a third device associated with a friend or family member of the first user. The server system generates the individualized application content using a plurality of digital therapeutics programs that each correspond to a different aspect of cancer treatment and cancer survivorship. The server system can be configured to generate the individualized application content using combinations of the digital therapeutics programs and user-specific sets of program states of the digital therapeutics programs for the first user. The method includes automatically varying, by the server system, the user-specific program states of the plurality of digital therapeutics programs to assign altered user-specific program states for the first user. The server system enforces interdependence of the digital therapeutics programs such that program states for the first user for at least some of the digital therapeutics programs are dependent on program states of one or more of the other digital therapeutics programs for the first user. The method includes distributing, by the server system, second individualized application content to at least the first device, the second individualized application content being generated for according to the altered user-specific program states.

Implementations can include one or more of the following features. For example, varying the user-specific program states comprises: automatically enabling one or more digital therapeutics programs for the first user such that the server initiates use of the enabled program to generate individualized application content for the first user; or automatically disabling one or more digital therapeutics programs for the first user such that the server discontinues use of the enabled program to generate individualized application content for the first user.

In some implementations, the program states correspond to different time periods representing sequential progression through a predetermined elements of the program.

In some implementations, the program states correspond to levels of interaction or levels of intensity of the digital therapeutics programs.

In some implementations, automatically varying the program states comprises automatically varying the program states according to sensor data generated by the first device, status information generated by computer systems of medical practitioners, and results of adaptive interactive forms customized for the first user.

In some implementations, automatically varying the program states comprises automatically varying the program states according to (i) at least one general data source providing one or more of weather data, points of interest data, or environmental data, and (ii) at least one user-specific data source from the group consisting of data from a wireless wearable device of the first user, data from a wirelessly connected medical device of the first user, electronic health records for the first user, prescription data for the first user, genetic data for the first user, social media data for the first user, and mobile device data from a mobile device of the first user.

In some implementations, the server system is configured to automatically vary the program states based on behavioral patterns of the first user, as identified by the server system based at least in part on sensor data acquired by the first device.

In some implementations, the method includes providing, by the server system, data for an administrator interface indicating the user-specific program states for multiple cancer patients or cancer survivors that are associated with the administrator. The administrator interface includes controls enabling the administrator to change program states that were automatically assigned by the server system.

In some implementations, the method includes setting and storing, for the first user, user-specific target levels for measures corresponding to the digital therapeutics programs. Automatically varying the program states comprises: identifying trends in the measures for the first user; and varying the program states based in part on the identified trends and the user-specific target levels for the first user.

In some implementations, the method includes: accessing a database of pharmaceutical data indicating cancer medications and effects of the cancer medications; storing records indicating cancer medications currently or previously used by the first user and current physiological data for the first user; evaluating applicability of the digital therapeutics programs for the first user based on the records for the first user, comprising: (i) determining current or expected effects of cancer medications currently or previously used by the first user; and (ii) determining scores indicating relationships between the determined effects and the digital therapeutics programs. Automatically varying the program states comprises varying the program states for the first user based on the scores indicating relationships between the determined effects for the first user and the digital therapeutics programs.

In some implementations, the server system provides digital therapeutics to each of multiple users, the digital therapeutics being determined according to a respective set of user-specific program states for each of the digital therapeutics programs for each of the user. The server system automatically varies the user-specific program states for each of the users based on each respective user's current situation and status.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 1B-1F illustrate examples of user interfaces that can be used to administer digital therapeutics and manage care plans.

Like reference numbers and designations in the various drawings indicate like elements.

DETAILED DESCRIPTION

Figure 1A:
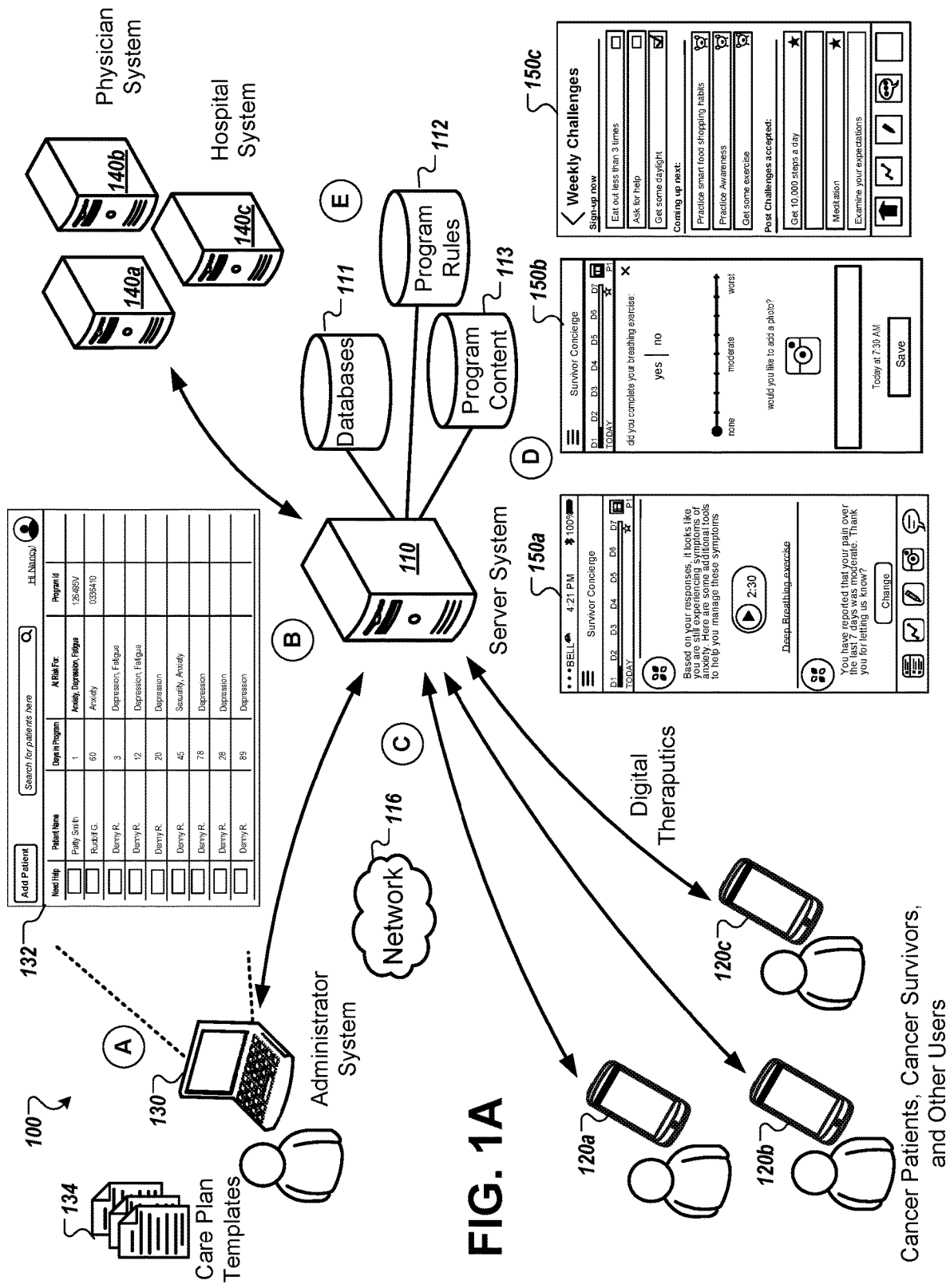
FIG. 1A is a diagram that illustrates an example of a system for generating and administering through dynamic individualized care plans.

FIG. 1A is a diagram that illustrates an example of a system 100 for generating dynamic individualized care plans. The system 100 includes a server system 110, client devices 120a-120c, an administrator system 130, and additional systems 140a-140c. The server system 110 communicates with each of the other components of the system over a network 116. The server system 110 also accesses a number of data collections, illustrated as databases 111, program rules 112, and program content 113.

The example in FIG. 1A shows various interactions that can be used to create, adjust, and carry out care plans. As an example, interactions shown in stages (A) to (E) follow a process of creating a care plan for a user, monitoring the user's status and needs, providing digital therapeutics, and adjusting the care plans for each user. The care plan provided by the system is not merely a statement of desired patient behaviors or treatments. Rather, the care plan provided by the system 100 is a real-time, interactive personalized medicine service that initiates communication and interaction with the user to deliver digital therapeutics. Among other effects, the digital therapeutics can involve interactions, initiated by the system 110 or by the user, that change the user's behavior, for example, to reach a goal such as losing weight, increasing sleep quality, reducing pain, and so on.

These user behaviors and outcomes that are affected are not merely behaviors interacting with devices, but often represent changes in real-world aspects of the user's life outside of human-device interaction. The digital therapeutics for a particular patient, and the timing for delivery, are dynamically selected and updated using a series of different digital therapeutics programs that can address different aspects of a patient's care. As discussed below, each program can have separate sets of content, rules, assessments, and interventions for providing a customized, adaptive experience for a patient. The system 100 can operate in an "always-on" manner, frequently or continually assessing a data stream indicating the user's current status and context, and providing targeted interactions that are relevant to the user's current or estimated future needs.

Throughout the discussion below, the person benefiting from medical care is often referred to as a cancer patient or cancer survivor in various examples. Nevertheless, the same system can provide benefits to other types of users, such as those who have not contracted cancer or those from whom cancer has not yet been detected. The system 100 can assist all types of users to enhance cancer prevention and early detection. Thus, care plans that provide dynamic, personalized digital therapeutics can be provided for healthy patients also. In this use, the server system 110 may identify and provide digital therapeutics that decrease risks of developing cancer and increase likelihoods of detecting early-stage cancer.

During stage (A), the server system 110 generates and provides an administrator portal 132, which may be provided as a web page, web application, data for a locally executable application of the administrator system 130, or in another form. This interactive portal 132 enables the administrator to view care plan templates 134 and select a template to use to enroll a new user. The portal 132 also provides controls for the administrator to modify the templates 134 for individual users, as well as view and alter care plans that are currently active for any of the users assisted by the administrator. An example of an administrator portal is shown in an expanded view in FIG. 1E. Examples of other information that can be provided, such as indications of goals and progress over time, are shown in a user interface 190 in FIG. 1F. The user interface 190 shown in FIG. 1F can be provided to an administrator, and in some implementations, to the user, to a family member of the user, a friend of the user, and/or a caregiver or medical service provider for the user.

The administrator portal 132 provides a number of care plan templates 134 that the administrator can select when enrolling a new user. In some instances, these care plans may correspond to different types of cancer, for example, one each for breast cancer, colon cancer, skin cancer, and so on. In other instances, the templates correspond to different phases of treatment, for example, cancer prevention, cancer treatment, or cancer survivorship. Templates may also be provided for healthy patients, for example, representing care plans to assist patients in minimizing risks of developing cancer and/or to increase the speed and accuracy of cancer detection and diagnosis of cancer.

The care plans can be generated as combinations of different digital therapeutics programs. A template 134 can specify a set of these programs that are made in active for a given patient. The programs each have a number of components and states that very how they interact with the patient. For example, each program may include multiple segments that are applicable over different time periods. The program can define a sequence of these segments, or multiple different sequences. The segments may correspond to fixed length periods, for example, a week, or month, or another fixed or standardized time period. Alternatively, one or more of the periods may have a variable duration.

Each program has various levels or intensities with which the program applies. The level of the program may affect, for example, how frequently the program communicates with the user, how ambitious or difficult the goals and activities of the program are, how closely a person's behavior is monitored, and so on. Different levels may correspond to different levels of patients need. For example, an alcohol use program may have a first level that helps a patient monitor and understand their alcohol use when it is well-controlled or in an acceptable range. A second level may provide more aggressive goal setting and motivation, with more frequent interactions to help the user reduce alcohol use. A third level may correspond to a more intense need for support in reducing alcohol use. For example, the program may interact with devices for friends and family members to more actively assist in helping a user meet their goals. In some implementations, different levels of a program, may respond to different clinical needs or conditions, but this is only optional.

When a person is first enrolled, the care plan template 134 selected by the administrator specify a default set of programs and corresponding levels for the user. The administrator may manually adjust the selections, for example, by adding or removing programs, and increasing or decreasing the levels of programs. In this matter, the administrator can specify an initial care plan that meets the needs identified by a doctor or other members of the user's support team.

With the interfaces and tools provided by the server system 110 through the administrator portal 132, an administrator can efficiently manage care plans for a large number of patients. In many instances, after the care plan is initiated, the administrator does not need to further modify or adjust the care plan. The server system 110 automatically adjusts each individual care plan according to the unique set of user inputs, sensor data, and behavior detected for each user. Nevertheless, an administrator can view an individual patient's progress and, if appropriate, adjust a patient's care plan manually through the administrator interface 132. As the server system 110 adjusts the care plans based on each users individual circumstances, different care plans will have different segments of programs, different levels of the programs, and different combinations of the programs active. These differences as well as the application of individual program rules to unique user data sets, provide a unique experience to each user.

During stage (A), the server system 110 stores information about each user enrolled in the system. As discussed further below, the server system 110 stores data indicating the current state of a user's care plan, such as the programs that are active, the levels of each program, which segment the user is currently in for each program, and so on. In addition, the server system 110 stores historical information about the user and his interactions with the application and progress while using the care plan. The server system 110 can acquire data from many different sources including the user's physicians, hospitals, surveys, sensor data, and other data discussed further below. This information can be stored in various databases 111.

During stage (B), the server system 110 also stores information that defines each of the programs. Each program can include a corresponding set of program rules 112. A repository of these rules 112 is maintained and accessed by the server system 110, and the rules are evaluated on an ongoing basis to determine when to communicate with each user and in what manner. If a user has multiple programs active, rules for each program separately can specify different communications or interventions to be provided to the user. Some examples include providing media to a user (e.g., text, audio, video, etc.) using the output devices of a user's device (e.g., display screen, speaker, vibrator, etc.), generating an interactive form such as a survey for the user, sending a notification email or other message, challenging, reminding, or informing the user about a goal, providing recommendations, providing content from a social media platform, providing instructional activities or games, and so on. These and other interactions can also be provided to friends, family members, medical service providers, and others to support the cancer patient or cancer survivor. For example, surveys or recommendations can be generated and sent to friends and family of a cancer patient or cancer survivor, to corroborate conditions indicated by the detected behavior or interactions of the cancer patient or cancer survivor. In this manner, the various programs can support the health of a user through interactions with one or more other associated users of the system. In some instances, these type of interactions may provide better results than direct messages to a cancer patient or cancer survivor.

The rules for the programs have conditions and triggers associated with them. Each rule may have a condition that must be satisfied for a corresponding system action of the rule to be performed. In addition, a rule can have a trigger or triggering condition associated with it, so that the action of the rule occurs when the trigger is satisfied as well as one or more other associated conditions.

The actions of the server system 110 to generate user specific interfaces and content can draw from a repository of program content 113. This repository 113 can include media, messages, and other content that is selectively provided according to the program rules in the repository 112, which in turn are selectively used according to which programs are active, which levels of the programs are active, and which segments of the programs are active.

During stage (C), the server system 110 obtains data for each of the various users enrolled with the care plan. The server system 110 communicates with user devices 120a-120c to acquire data for each of the various users in rolled with the care plan. The server system 110 communicates with user devices 120a-120c to acquire context information, such as the location of the user, a current activity of the user, sensor data, and other data. The server system 110 also communicates with third-party systems to access medical records, data about recent doctor visits, and even general information such as current news, weather, and other data.

In stage (D), the server system 110 applies the individual care plan for each user to the data collected for the user. For example, the rules that are applicable to an active segment of an active program are evaluated using the context information historical information and other data. And this allows the system and 110 to determine, for this particular program and this particular user at the current time, what information should be requested through a survey perhaps or what information should be provided to the user. This is done for each of the programs that are active in the users care plan. The server system 110 takes all of the results of the different programs in the care plan and generates customized user interface data to be sent to the appropriate use your device of the user. Although different programs may indicate different messages to be provided or different survey questions to present to her user, the server system 110 may integrate the content across the various programs.

Figures 1B, 1C:
Figure 1F:
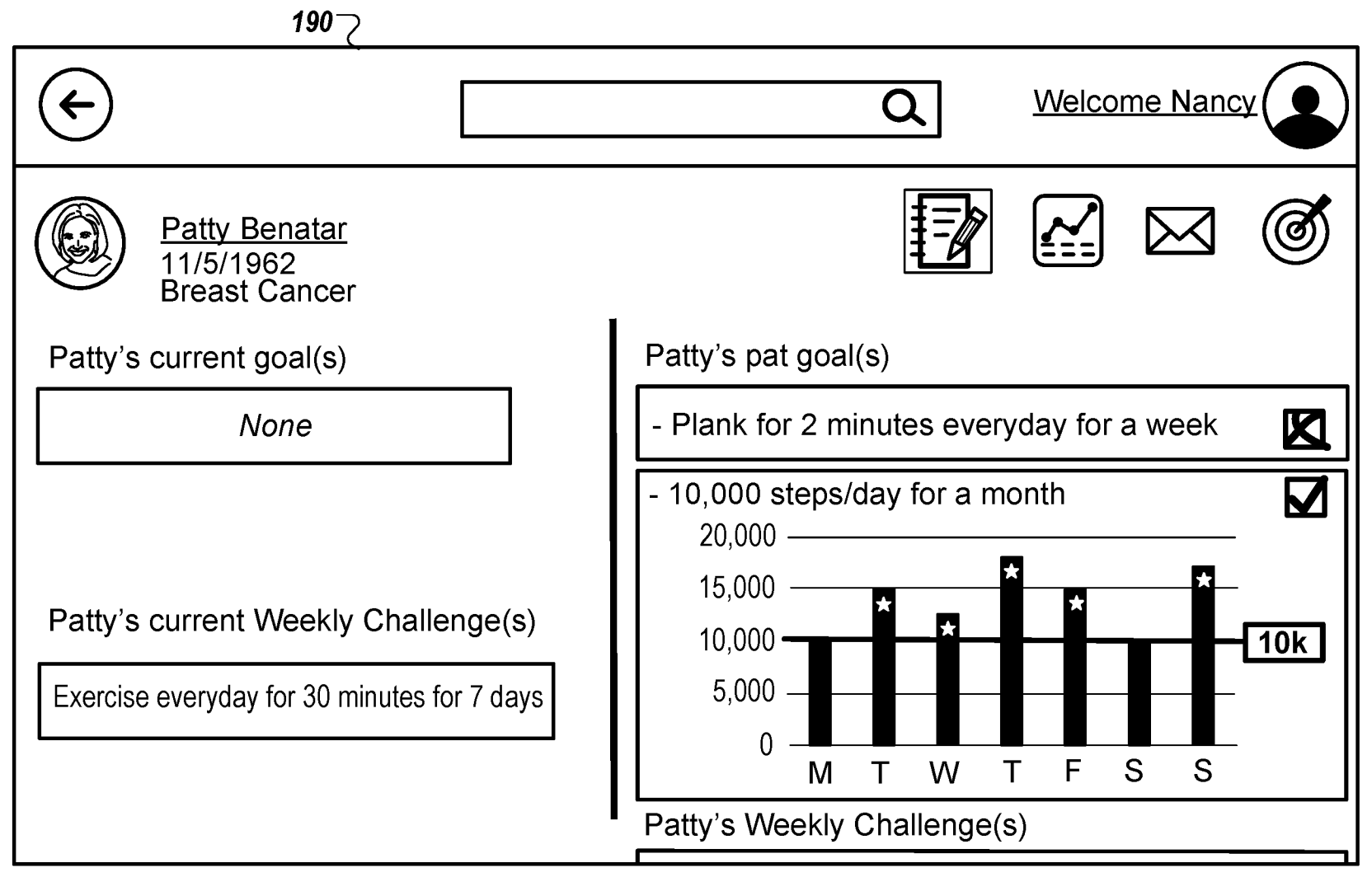

As the user interface data is provided to the user devices 120, users interact with the digital therapeutics care plan application on their devices 120. Data indicating inputs to the application and the manner in which the user acts in response to the communication are determined and provided to the server system 110, which logs this information. For example, if a user is shown a message recommending they go outside and take advantage of the good weather, and subsequently does go outside as detected by motion sensors and location sensors of the device, the server can store this information and use it to determine future content for the user. Examples of user interfaces showing user interfaces that may be provided on the user devices 120a-120c are shown in elements 150a-150c, which are shown in an expanded view in FIGS. 1B-1D.

During stage (E), the server system 110 adjusts the states of the programs if appropriate. The server system 110 can assess various factors to determine whether the set of programs that is active should change, and whether the levels and active segments of each program should change. In some instances, a user progresses through segments of a program based on the passage of time. The server system 110 can detect when an appropriate transition from one time. To the next occurs, and so when the change in applicable rules occurs.

Transitions between levels of programs can be based on the performance of the user with respect to certain targets for goals, which may be standardized for the month program or maybe user specific. For example, a program for physical activity may set a goal of a number of steps per day for the user to walk. When a user successfully completes ago the system may determine that a level corresponding to a higher goal is appropriate. In some instances, a higher level represents a need for greater intervention or monitoring. As a result, or user who successfully completes goals for physical activity may be transitioned automatically to a lower level of the physical activity program in which fewer reminders or interactions are provided, since the user has shown the ability and willingness to exercise. On the other hand, are user who is not exercising to the extent needed, or who is not responding to the interventions of the program may be transitioned to a higher level indicating more intense or different types of interaction in an attempt to improve the users physical activity.

As another example, a user that would like to reduce alcohol use may begin at a second level of an alcohol use program. Over time, as the user demonstrates improvement (e.g., he has learned important principles of alcohol management as shown through tracking and surveys, and whose alcohol use has begun to decline as indicated by survey responses), the program may then be transitioned to a lower level. Continued progress in reducing alcohol use may result in further reducing the level, as well as setting a more aggressive goal. Eventually, interactions related to alcohol use may become less and less frequent as the user demonstrates that those interactions are not needed. For example, after discontinuing alcohol use and indicating on several surveys over time the alcohol is not used, the alcohol use program may be deactivated entirely.

Thus, by varying the level of each program as a user progresses through the program segments, the server system 110 can tailor the degree of interaction and intensity of support across various aspects of the user's wellbeing and lifestyle.

When adjusting the programs in a care plan, the levels or states of the programs can be interdependent. Changes in the level of one program may result in changes to other programs. These interdependent level transitions may depend on more than simply the levels of other programs, and maybe based on any of the data collected from or about a user as well, as well as any of the outputs of the different programs.

One of the ways that the server system 110 interacts with users is to provide interactive forms and surveys. Each form can be customized or dynamically created for a user's current status and the current state of his care plan. These forms can request information that is indicative of the user's wellbeing or progress with respect to one or more active programs in the care plan. Similarly, the surveys may include questions or other interactive activities that would enable the server system 110 to evaluate whether additional programs should be activated. The server system 110 may use a variety of computer adaptive testing techniques to generate forms that acquire sufficient information needed to determine her use of progress for various programs, without overburdening the user.

As an example, each of the programs that are active in a user's care plan may indicate, periodically or intermittently, types of data needed from a user. Even for a single program, the type of data needed may vary over time. For example, different segments of a program may correspond to different combinations of topics. Different levels may require different frequencies of input or different precision of input. Thus, each program may provide a list of data items to obtain from a user. The server system 110 and may assess these lists to generate appropriate interactions that obtain the appropriate information and benefits the user.

The server system 110 may de-duplicate the set of data items so that multiple redundant questions are not asked. The server system 110 also checks recent answers and interactions of the user, as well as any other data sources (e.g., location data, sensor data, medical records, communications of family and friends with the server system, etc.) to determine if the requested information is available from other sources already. For the remaining items that are not yet available, the server system 110 may prioritize or schedule the data acquisition to reduce the overall burden of any one interaction and increase the likelihood that the user will complete the form successfully.

The server system 110 may group the remaining data items into related groups. For example, the data needed by multiple programs may be acquired through a single form, and in some instances multiple items of data may be able to be obtained through a single question.

The server system 110 can access a database of questions and interactive activities, with each item having metadata specifying the types of data obtained through the question or activities. Thus, by mapping needed data types to the various types of interactions in the database, the server system 110 selects a few questions or interactions that can acquire the needed input.

The server system 110 may implement the survey or form generation process to allow significant flexibility. Individual programs may provide fully formed questions or interactive elements to be incorporated into a user interface. In addition, or as an alternative, programs may simply provide an indication of data types to be acquired, and the system 110 can formulate appropriate questions and user interface elements for obtaining the data. As noted above, the server system also may combine and integrate the requests needed by various programs. The server system 110 may also generate data for user forms through any of the techniques discussed in U.S. patent application Ser. No. 15/279,845, filed Sep. 29, 2016 and titled "Customized Dynamic User Forms," which is incorporated herein by reference in its entirety.

In many cases, the questions and interactions in a survey are adapted to normal daily life of the user. For example, a cancer survivor may not benefit from being constantly reminded that they are expensive survivor. As a result, the server system 110 may provide digital therapeutics and request information through day-to-day interactions that are not necessarily cancer-specific. For example, valuable information can be obtained through journal entries a user enters in association with the application. The application can ask about the user's plans for the weekend, recommend a friend to reach out to, assist with fitness goals and tracking, and generally provide daily assistance. Although these interactions may not relate specifically to cancer treatment or survivorship, the content provided to a user and data obtained from the user in this manner can be used to carry out and update the care plan.

The data the server system 110 obtains can directly affect which interventions or interactions are provided, which programs are active and to what extent, the assessment of various risk levels for physical or psychological conditions, and so on. In many cases, simple recommendations or questions by the server system 110 can be targeted directly to alleviating symptoms or risks occasioned by current or former cancer status. For example, when the server system 110 detects data indicative of anxiety or low energy, the server system 110 can provide an indication of the current weather and encouragement to visit a nearby state park. The rules of one or more programs may take into account that sunshine and physical activity are likely to address symptoms of depression anxiety or low energy. In fact, through analysis of symptom levels and activities of other patients at a similar stage of cancer treatment or survivorship, the server system 110 can set or adjust rules specifying when this suggestion should be provided.

In addition, the system may obtain information in ways that do not require explicit entry of an answer to a question. For example, if the system provides a content for user, the system can assess whether the user completes viewing the content, which areas the user spends the most time viewing, which links are selected, and so on. These can provide valuable information that indicates a user's level of engagement, mood, etc. Similarly, a user's performance in a game may indicate the user's reaction time, language capabilities, mood, and so on.

The server system 110 may cause many different types of interactions and digital therapeutics interventions to be provided to a user. For example, the system 110 can cause a device to perform any of the following actions: prompt a user to provide a journal entry or to view a prior journal entry; record a measurement from one or more devices; provide a survey or question for a user to answer; provide content for a user to read or view; initiate a challenge for a user with a defined time frame (e.g., a daily, weekly, or monthly challenge goal or competition); prompt a user to set, adjust, or view a personal goal; communicate with family, friends, or others regarding a user's goals or status; and initiate a call, message exchange, or real-time text chat with a health service provider. The actions taken by the system can provide educational information and activities to improve a patient's knowledge. The actions can provide motivation or encouragement to increase positive behaviors or decrease negative ones, for example, prior to a user performing a desired action. The actions of the system can reinforce positive behaviors, for example, by providing positive messages, rewards, or activities after a desired behavior is performed. These and other actions of the system can be performed as directed by the digital therapeutics programs that are active for the patient, with each active program potentially providing different interactions at different times. The interventions of the programs can be tailored to achieve any of various results, including adherence to a clinical regimen, behavior change, patient education, and so on.

In general, the system 100 can be used to provide a variety of digital therapeutics, which are not limited to supporting cancer patients and cancer survivors. For example, a few of the diseases or disorders that the system 100 can be used to treat include heart disease, diabetes, lung disease, immunological disease, mental disorders, chronic pain, and bone disease. While users with these conditions have needs that are different from those of cancer patients and cancer survivors, they can nevertheless benefit from the adaptability and total-body wellness support that the system 100 can provide. Similarly, the system 100 can provide support over any and all of a continuum of care, for example, prevention, diagnosis, treatment, and post-treatment.

Figure 2:
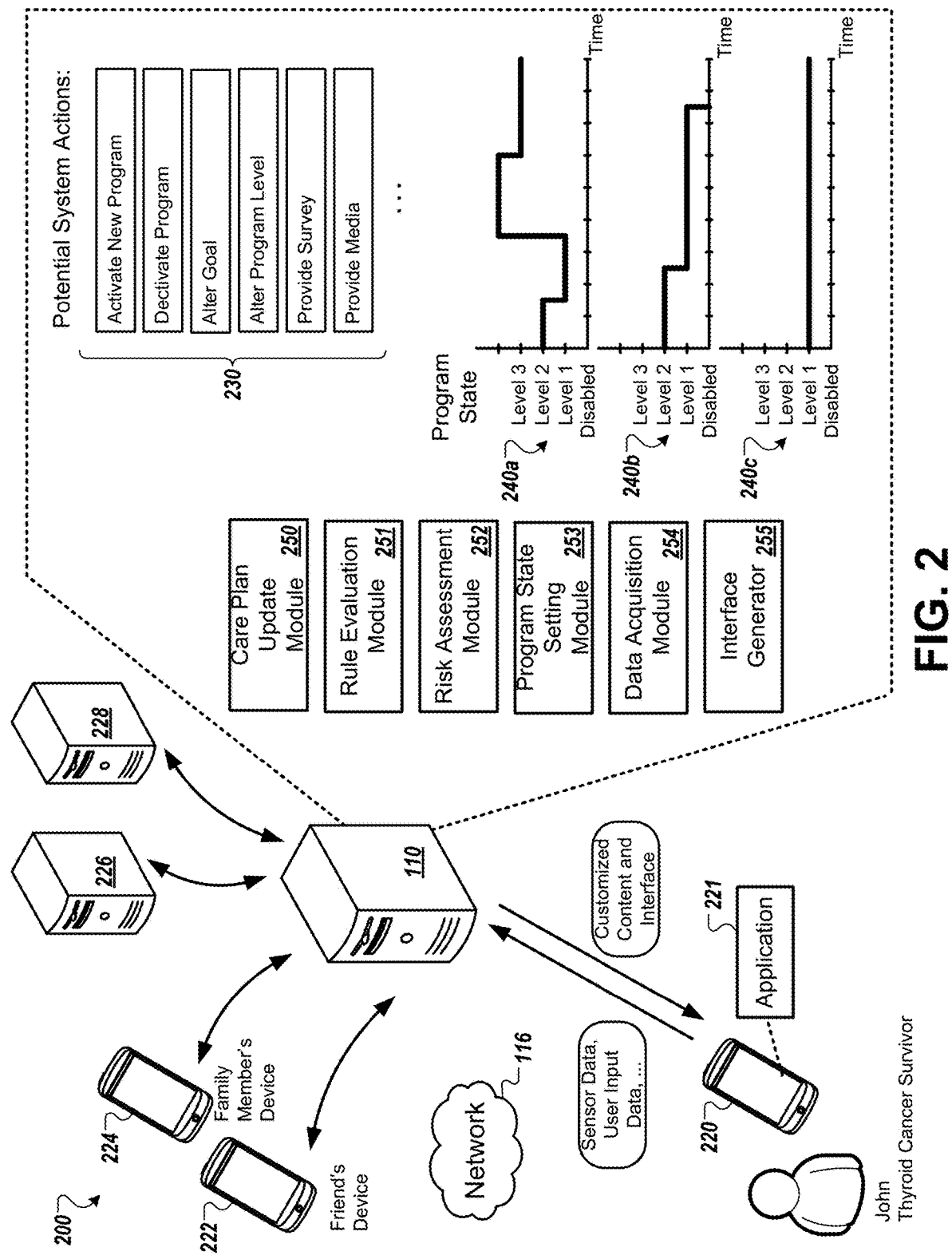
FIG. 2 shows an example of a system for providing digital therapeutics to a cancer survivor or cancer patient.

FIG. 2 shows an example of a system 200 for providing digital therapeutics to a cancer survivor or cancer patient. As discussed further below, the server system 110 is able to adjust and adapt the care plan for the patient, and also provide direct interventions and supports to help a patient meet goals of the care plan.

In the example of FIG. 2, a user named "John" is a thyroid cancer survivor and has a mobile device 220. The user has previously been enrolled to a care plan by an administrator. John's mobile device 220 has an application installed that helps carry out the interactions and interventions of the care plan. For example, the application 221 may collect sensor data and user input from the device 220 and other devices nearby on an ongoing basis. The application 221 provides this data to the server system 110 for storage and analysis. As the server system 110 applies the appropriate rules and programs of John's care plan, the server system 110 periodically sends customized content and interface data to the mobile device 220 to be displayed through the application 221 or interacts with the mobile device 220 in another manner.

In general, the care plan can push content to the mobile device 220 for display as triggered by the rules of the various programs active in the care plan. Rather than the user manually requesting content, e.g., by opening the app to 214 navigate to a web page, the server system 110 and/or the app 221 can initiate intermittent and unexpected interactions throughout the course of a day, week, etc. In a sense, the interactions of the care plan can be generated through a kind of always-on or continuous analysis by the server system 110. For example, for a user who is trying to achieve a goal of reducing alcohol consumption, location data indicating that the user is near a bar may trigger the system to provide, at that time, helpful information, such as a reminder of the user's current goal, praise for recent progress, or information about measuring drinks. The programs of a care plan can, in this manner, provide contextually relevant interactions at any time, as determined appropriate by the server system 110 from the various data sources available to the server system 110.

The server system 110 communicates with the mobile device 220 over the communications network 116. To carry out the care plan, the server system 110 may also communicate with various other devices and third-party systems. For example, the care plan may include information about friends and family members of the user, John, and phone numbers, email addresses, device identifiers, or other information that enables the server system 110 to interact with them. For example, the server system 110 may communicate with a family member's device 224 and friend's device 222, as just a few examples. Just as the system 110 can provide occasional surveys or interactive activities to the user, John, server system 110 can also generate customized surveys and activities for friends and family of the user. These interactions can provide confirmation of data that the user provided, and/or different types of data, such as information that the user may not personally be aware of.

The server system 110 also interacts with third-party systems, illustrated as computing systems 226 and 228. These systems 226 and 228 represent any of a variety of public and private data sources. For example, they may represent computing systems for the user's physician, insurance company, social media network, calendar provider, or other service. Additionally, the systems can represent sources for other data, such as weather data, environmental data such as pollution levels, upcoming events data, map data, and so on.

As noted above, the information obtained can include various types of health data. For example, EMR/EHR can be obtained from medical providers. Records of appointments and test results can also be obtained. Information indicating a family medical history, a genetic profile for the user, current and former medications, and other health records can be obtained and stored by the server system for each user.

As a result, the server system 110 may interact with a first device, e.g., device 220 for a user that represents a cancer patient, cancer survivor, or other user receiving digital therapeutics from the system 110. The system 110 can also interact with a second device associated with a caregiver of the user, such as a device of a health service provider (e.g., physician, nurse, coach, psychologist, physical therapist, etc.). The system can also interact with a third device, e.g., device 222 or device 224, associated with a friend or family member. Each of these devices can run an interactive application that supports the provision of digital therapeutics to the user, e.g., John, receiving digital therapeutics. All of the device may receive surveys, educational information, and other interactive activities. For example, when information is needed, or when compliance with a treatment regimen or goal needs to be verified, a caregiver or friend or family member may be asked in addition to or instead of the patient. In some implementations, friends or family members may remotely view some information about the patient, including goals, progress toward goals, status information, and an indication of which programs are active. This information may be subject to consent of the patient. A caregiver may be provided this same information as well as indications of levels of programs, recent interactions, and other data gathered by the system. The caregiver's interface through the application may further allow the caregiver to set goals or change the states of programs, while the interface for friends and family may not allow these changes.

With input collected on an ongoing basis from these data sources and others, the server system 110 applies the rules of each active program in the user's care plan. These rules can specify various different system actions to be performed. The server system 110 can administer programs and evaluate rules using any of the techniques discussed in U.S. patent application Ser. No. 15/337,222, filed Oct. 28, 2016, and/or U.S. Pat. No. 9,753,618, issued on Sep. 5, 2017, both of which are incorporated herein by reference.

The incoming data stream regarding a user, compiled from all available data sources, may be used to form a current data set or profile for the user. The server system 110 continuously updates the profile representing the user's current status, using all of the various input data sources.

Among the various actions that the server system 110 can perform are actions that alter or adjust the combination of programs in a care plan and the program state or level of individual programs. For example, the server system 110 may evaluate the incoming stream of data about a user, and extract specific data types and measurements relevant to each program. The rules that are applicable at a given time can specify the types of data that are needed for a program. For example, of the rules of a program, only a proper subset of the rules may be applicable to the current level and segment of the program. The server system 110 can identify the set of data needed to determine whether the conditions and triggers of the rules in the subset are satisfied.

Each program may have, in its corresponding set of rules, one or more rules setting conditions and triggers for altering program state. These factors may be unique to each program, and to each level transition. That is, a first program relating to physical exercise may have different sets of rules that govern whether to transition from level 1 up to level 2, from level 2 up to level 3, from level 3 down to level 2, and so on. In some instances, changes in program state may occur at any time that appropriate conditions and triggers are met. In other instances, changes in program state may occur at transitions between segments or at other specified intervals.

In the example of FIG. 2, charts showing program states over time are shown for three different programs 240a-240c in John's care plan. The program states vary over time due to the server system 110 determining that more or less intervention is needed for corresponding topics at different times. The transition decisions are made based on rules of the programs applied to the current user status profile at the specific point in time when those transitions were made. As illustrated, the state of the first program 240a varies significantly over time. This may represent for example, variations for a pain management program responding to highly variable amounts of pain experienced by user. The second program 240b shows a gradual decrease from level two, to level one, and then disabling the program. This may represent, for example, steady progress of the user to the extent that the rules of the program specify that no further support is needed. For example, a user that was initially using a sleep disorder program may have his or her sleep patterns normalize over time, to the extent that no further support is needed. The third program 240c represents a constant level over the time period. This may indicate, for example, that a user is maintaining acceptable performance, but not be meeting goals sufficiently to reduce the level. On the other hand, certain programs, such as those for nutrition and physical exercise, may be included as a matter of course on a certain level or state since they are components of a healthy lifestyle regardless of a user's current performance.

Because cancer has so many effects to the body and to a person's lifestyle, the programs can be interdependent. The state of any given program may depend on the state of one or more other programs, or even all other programs in the care plan. Various techniques may be used to provide this interdependence. For example, program rules that specify system actions to be performed under certain conditions may specify that certain states of certain programs are a condition or trigger for a level transition. Similarly, the act of making a program active in a care plan or transitioning to a different level of a program may be a condition or trigger. For example, activating or increasing a level of a fatigue program may trigger the activation of a sleep disorder program at a first level, if the sleep disorder program is not already active. Thus, if the server system 110 detect increased fatigue from the user's profile, the server can transition to a greater intervention level for the fatigue program, and also initiate sleep monitoring and analysis, even if sleep disorders have not been diagnosed or indicated from data about the user.

As another example, the output of a program may be used to set levels/program states of other programs. For example, the server system 110 can assess the types of survey questions or data types that programs use. Each program may include a specification of data types that are assessed using the program, or the specification can be inferred from the rules of the program. If a program is disabled but has a specification indicating data types that match those being requested by other programs, the disabled program may be activated. In other words, analysis of content provided to a user by programs, and data input requests of other programs, can be used to determine a relevance score between current interactions with the user and the other programs. When the relevance score satisfies a threshold, this may trigger the activation of a program or an increase in the level of a program.

In some implementations, relationships between programs may be predetermined, e.g., manually defined or explicitly set through rules. This is not required, however. Indeed, the analysis of the combined program states in a care plan and/or the outputs of the programs to a user can be effective to adjust program states even with no specific knowledge of interconnections between the subject matter of different applications/programs. The server system 110 can infer relationships through commonalities in program specifications and outputs of the programs. That is, the patterns of outputs of a program and requests for inputs by the program can show over time in the manner in which the program relates to other programs. The server system 110 may analyze these relationships, for example, comparing which segments of programs and which levels of programs relate to specific levels and segment of other programs. The system 110 can also apply machine learning techniques, such as reinforcement learning, to patterns of care plan creation, level transitions over time, and other factors. With a sufficient data set generated from the progress of many users, the server system 110 can identify typical patterns in user status profiles, with the corresponding combinations of programs and levels. As the system 110 assesses program state transitions over time, the server system 110 is able to identify combinations of programs and levels that produce the best results for users with specific backgrounds. For example, the server system 110 may identify, for each of multiple different cluster of symptoms, which combinations of programs, and at what levels, are most effective at reducing the symptoms over a time period, e.g., a week, a month, a year, etc.

For example, the server system 110 may evaluate user status profiles and corresponding program states over a period of time, and determine that users that have three particular programs active simultaneously have the highest likelihood of achieving a decrease in the level of a fourth program. From this determination, the server system 110 may generate rules that activate the three programs together if the fourth program is active. More complex conditions may be set if desired. For example, rather than activate all three programs, the change may be limited to activating only one of the programs if two of the three are already active and the fourth is also active. As another example, all three programs in the group may be activated if the level of the fourth program is above a threshold, but not if the level of the fourth program is below the threshold. Of course, the behavior learned of the server system 110 does not need to be expressed in explicit rules and can, in various implementations, be incrementally learned as part of a training state of a classifier, neural network, or other machine learning model.

In general, the server system 110 can use a variety of interactions, measurements, testing, biomarkers (e.g., physiological readings, blood test results, genetic information, etc.) and stated or observed behaviors of a user to set program states. The server system 110 can use these same factors to select which digital therapeutic interventions to provide to an individual user, and when and how to provide them. In addition, the server system 110 can identify digital biomarkers and use them as indicators for selecting certain digital therapeutics. Certain combinations of data about a patient's activities and lifestyle can indicate health status and health risks of a user, just as the user's blood chemistry, genetic profile, and other observable physical traits may indicate health status and health risks. Similarly, data that the server system 110 collects about a user's activities and preferences, in combination with information about physical traits, may serve as digital biomarkers that provide more accurate predictive information than the physical traits alone.

As an example, the server system 110 may define a particular biomarker to represent a patient having a certain gene or combination of genes, with a sedentary activity profile, and certain diet characteristics. This combination of factors may be known to provide increased risk for cancer or other health conditions. When a user is determined to have this combination of factors, the server system 110 may input to the various digital therapeutics programs that the digital biomarker is present. The various programs may then respond with interventions tailored to alter the behaviors that cause the digital biomarker to be present, or to encourage other behaviors that decrease the risks associated with the digital biomarker.

The server system 110 may evaluate various data sets to determine which combinations of data about a user constitute a digital biomarker that is predictive of health outcomes. For example, the server system 110 may access data sets for longitudinal studies that show data collections describing many individuals, their characteristics, and their health outcomes over time. From analysis of this data, the server system 110 can select combinations of characteristics and actions that satisfy a minimum threshold of relevance to different health outcomes, and define the identified combinations of data factors as digital biomarkers. In some implementations, digital biomarkers can be defined in terms of digital therapeutics programs and their states. For example, by analysis of users of the system 100 and their health outcomes, the server system 110 may identify combinations of programs and levels that, when active may represent certain risks, when taken alone or in combination with physical health traits. Accordingly, the server system 110 may define these combinations of programs and states as biomarkers that may be used to alter the combination of states, for example, to add a particular additional program to reduce the risk of a future complication.

The server system 110 performs a variety of functions in creation and administration of the dynamic, individualized care plans. A few of these functions are represented in FIG. 2 as various modules of the server system 110. While the various functions are illustrated separately for clarity in illustration, various implementations may combine these functions into a single module for a different grouping of modules.

A care plan update module 250 can modify the care plan for each individual user, for example, based on changes in medical status of the user or manual entry from an administrator through the portal discussed for FIG. 1A.

A rule evaluation module 251 can select, from each active program of a care plan, the appropriate rules corresponding to the current segment and level of the program. Then, the rule evaluation module 251 compares aspects of the user's status profile with the triggers and conditions of the selected rules. The rule evaluation module 251 causes the system actions corresponding to rules with satisfied triggers and conditions to be performed.

A risk assessment module 252 can determine the unique risk profile of a user given the user's current profile and historical data. Cancer patients and cancer survivors often have drastically different risk profiles compared to others. From one cancer patient or survivor to the next, the risks maybe similarly diverse. As an example, a patient that has undergone radiation therapy may have a higher risk of incidence of later cancers of other types. As another example, a breast cancer survivor may have a much higher risk of adverse health effects due to alcohol consumption then a person that has not had breast cancer. A person's lifestyle, exposure to environmental factors, genetic profile, family medical history, and many other factors result in unique risk levels for individual patients. Because the server system 110 collects and stores information for these factors, the server system 110 can calculate the individualized risks based on the data set compiled for the user. To aid in generating these risk levels, the server system 110 may store and access clinical data sets representing outcomes and statistics representing many different groups of people. From clinical data and statistical analysis of the data sets, the server system 110 can determine a baseline risk level as well as a large set of factors that increase and decrease risk. The server system 110 identifies which of the many factors are applicable given a user's current profile and historical data and adjusts the baseline risk accordingly. In this manner, risk levels can be generated for many different conditions, e.g., pain, depression, recurrence of cancer, reduced sensory ability, etc.

The risk assessment module 252 can determine an individual's risk with respect to a set of potential outcomes and update those as the person's profile changes. Similarly, as the server system 110 receives new clinical data or as user outcome patterns are observed for the users of the system, the risk levels are also changed. The risk levels determined by the risk assessment module 252 may be used in a number of ways. In some instances, a person may be informed of their risk level and how it compares to other cancer patients or survivors, or to other people in general. As another example, the risk levels may be provided as input to the rules of various programs, provided as input to the rules of various programs, which may condition they performance of certain system actions on risk levels in certain ranges. For example, a risk level for reduced mobility may be calculated and provided as an input to a program for physical exercise, which may increase or decrease its level based on that risk level. Risk levels for a patient may trigger the activation of a program or increase in the level of a program, e.g., if the user's risk of experiencing an associated condition is above a threshold. Similarly, risk levels can trigger the deactivation of a program or decrease in the level of a program, e.g., if the user's risk is below a threshold.

The program state transition module 253 may govern transitions in program state for a person's care plan. As discussed above, changes may be made due to the interaction and execution of rules for different programs. In addition, or as an alternative, a module of the system 110 may be used to manage these changes. This module 253 man initiate changes in programs based on analysis of a user status profile and current and previous program states for the user. The program state transition module 253 may limit or normalize changes indicated by program rules. For example, the program state transition module 253 may enforce certain restrictions, such as limiting a frequency of level changes that are allowed over a period of time. An advantage of using the program state transition module 253 to initiate program state transitions is the ability to apply analysis for the care plan as a whole, rather than just as the rules of a single program within a care plan. As a result, the program state transition module 253 can enforce various aspects desired for care plans, whether determined using manually set rules, administrator preferences, relationships learned through analysis of stored data, and so on.

The data acquisition module 254 coordinates the requests for information from devices 220, 222, 224, 226, 228, and others. This data acquisition module 254 may obtain a list of requested data types or questions from the various programs, assess them to condense into a final set of needed information, and schedule interactions to acquire the needed data. Similarly, the data acquisition module 254 may periodically request sensor data, medical records, weather data, and any other applicable type of information needed from various systems to allow the rules of the programs to be evaluated.

An interface generator 255 produces data packages that are sent to the application 221 on the mobile device 220. The interface generator 255 specifies content to be provided on the user interfaces of the application 221, which may include various combinations of media, text, data entry elements, and so on. When a module specifies that certain content should be provided, the interface generator 225 receives the indication, determines the content layout formatting and so on that are needed. Through the interfaces that are generated, the system provides many different types of interactions with users. For example, the programs and other elements of the system 110 may cause a survey to be provided, provide media to the user, provide instructional materials, provide a test, provide a game, or initiate other activity with the user. Further, the interface generator 255 can specify interactions beyond interactions with a visible display. Interactions can be specified to involve audio output, voice input, haptic output, gesture input, and other input/output modalities.

Figure 3:
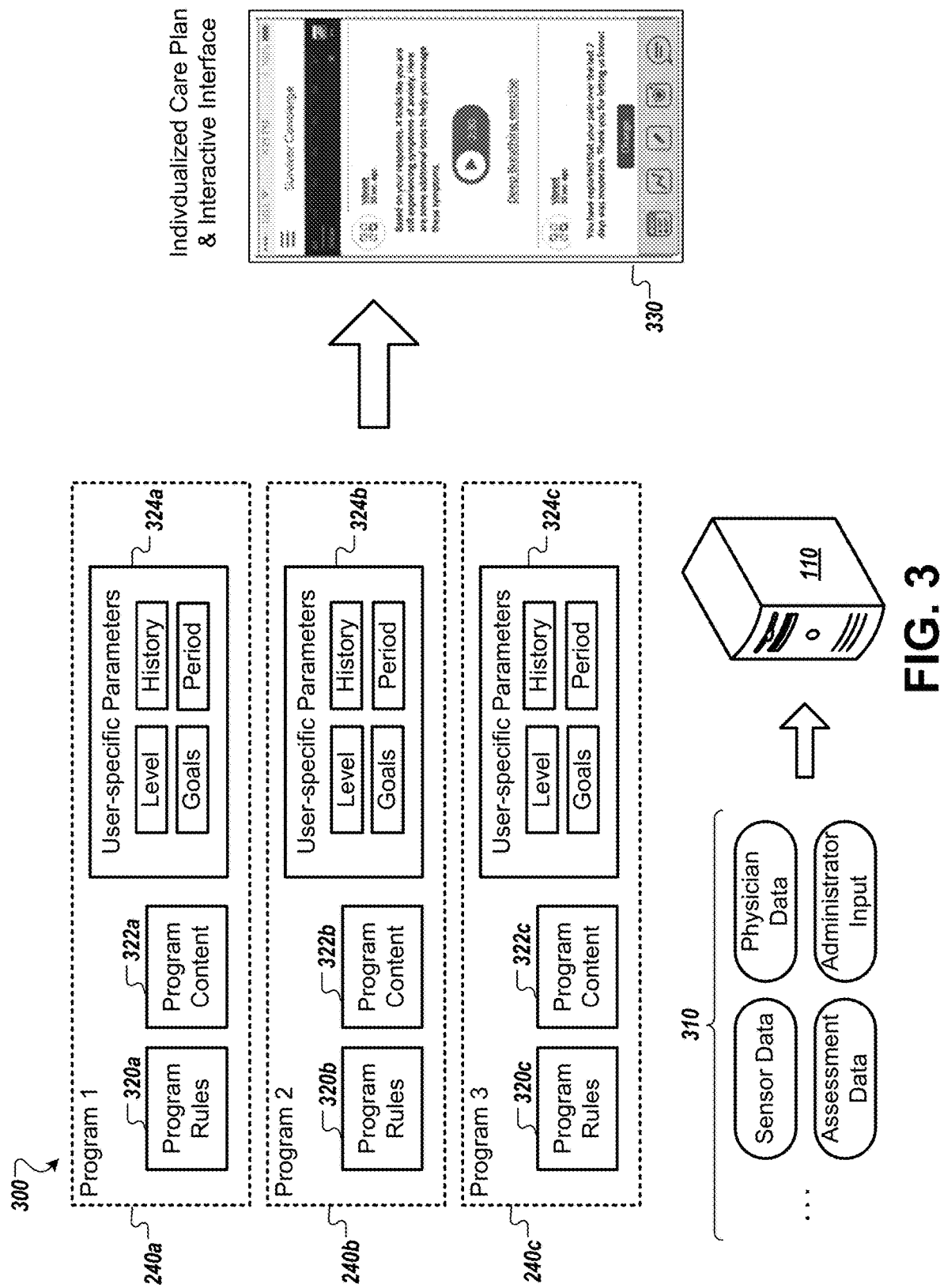
FIG. 3 is a diagram that illustrates examples of data used to generate dynamic, individualized care plans.

FIG. 3 shows additional data that the server system 110 can use to generate dynamic, individualized care plans. The figure shows the three programs from FIG. 2, with an indication of stored data and user-specific parameters for each.

Each program includes a set of program rules 320a-320c. The overall set of rules for a program are generally applicable to all users of the program. However, as discussed above, different subsets are applicable to different users at different times. Further, of the applicable subset of rules, only certain rules will have their conditions and triggers satisfied at any given time. Rules may be marked with metadata or may include elements specifying which levels and segments of a program each rule corresponds to. This can allow the server system 110 to filter, for each user, the overall set of rules for the program to a smaller subset to actually evaluate for the user. This can greatly increase efficiency and reduce computation, especially when the server system 110 supports a very large number of users simultaneously.

Each program includes a set of program content 322a-322c. This content represents source material from which individualized interactions with a user are generated. For example, the content for a program may include questions, videos, audio segments, images, instructional materials, messages (e.g., indicating encouragement, reminders, etc.), games, and other content. When indicated by the program rules 320a-320c, specific portions of the content may be accessed, combined into a data package for the user, and provided by the server system 110 to the mobile device 220 for presentation to the user.

Each user's care plan includes user-specific parameters 324a-324c for each program. These include the current level of the program, current goals of the user for the program, historical information about the program, and an indication of the current period or segment of the user in the program. The user-specific parameters 324a-324c specify how the programs 240a-240c process the input data 310, and ultimately how the individualized care plan and interactive user interfaces 330 are determined for each user.

The level can represent a level of need or intensity of needed interaction for the topics or categories of that program. Thus, a higher level may indicate more severe symptoms or greater need for contacting support through the airport. This is optional, however, and levels may have a different meaning. In some instances, a high level may indicate greater progress, for example, goals in an advanced range, achievement of certain skills, or other positive attributes. For example, for a physical exercise program levels may be set up so that users in higher levels have more difficult goals to meet and/or have progressed to significant measure through the program. For example, in some cases finishing all segments of a program successfully and meeting associated goals, may indicate that the user no longer needs the program. In other instances, success in reaching the goals may result in a change in level that requires or allows objectively more difficult goals.

The server system 110 is also shown receiving a set of input data 310. This input data 310 can be used to determine the current status of a user or historical information about the user. Input data can be actively requested by the server system 110 from a user device, another server system, or other device. Input data can also be passively received, e.g., periodically sent or broadcasted by other devices. As discussed above, the input to the server system 110 can include may different sources including sensor data from a user's mobile device or other devices, assessment data (e.g., survey responses, test results, etc.), input from administrators, data from physicians, weather data, points of interest data, or environmental data, data from a wireless wearable device, data from a medical device, electronic health records for the user, prescription data for the user, genetic data for the user, social media data for the user, and mobile device data from a mobile device of the user, to name a few. Other types of data used by the server system 110 in carrying out the programs 240a-240c and adjusting the states of the programs 240a-240c is discussed with respect to FIG. 6.

Figure 4A:
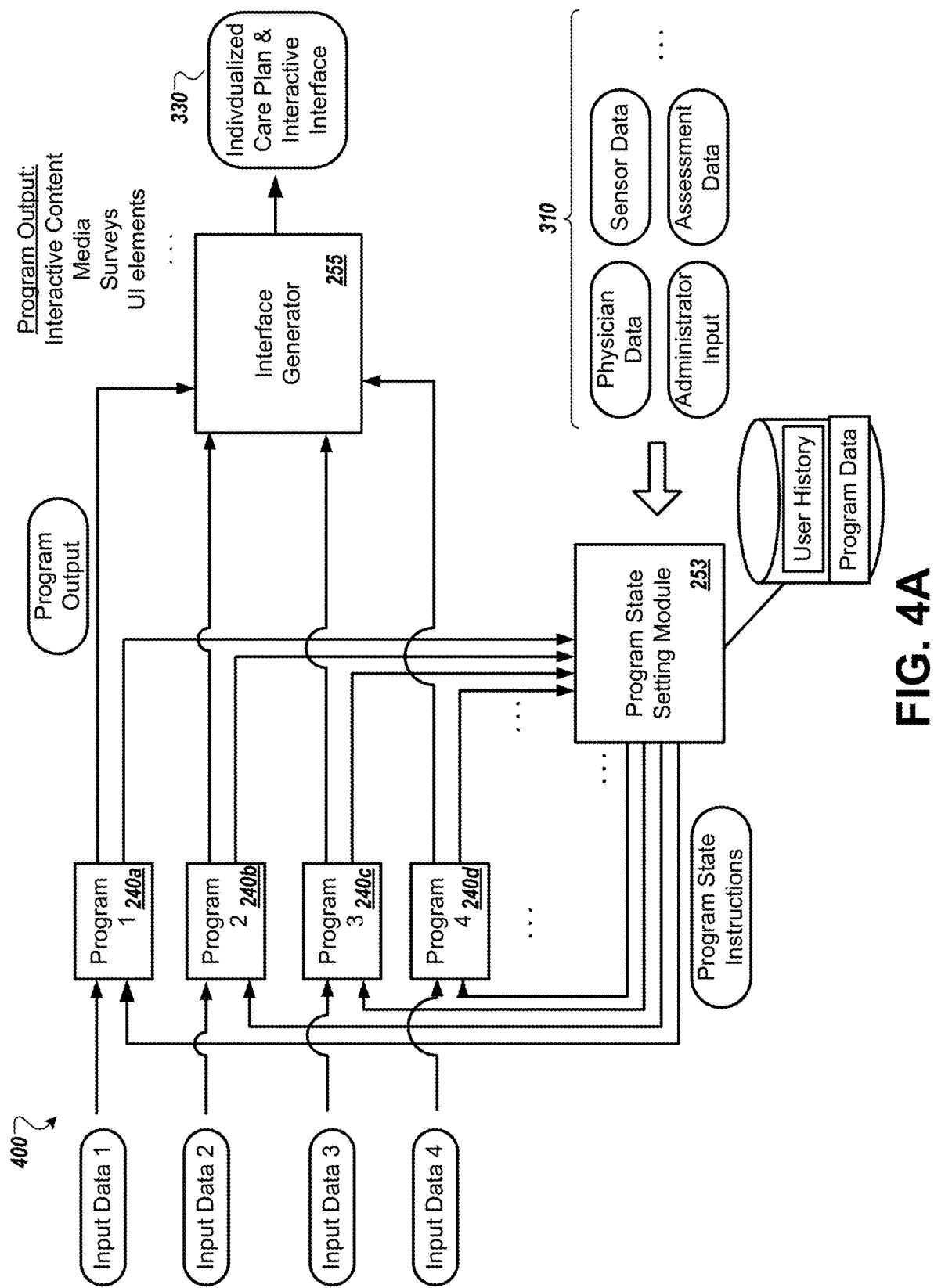
FIGS. 4A-4B are diagrams that illustrate examples of techniques for adjust states of digital therapeutics programs
Figure 4B:
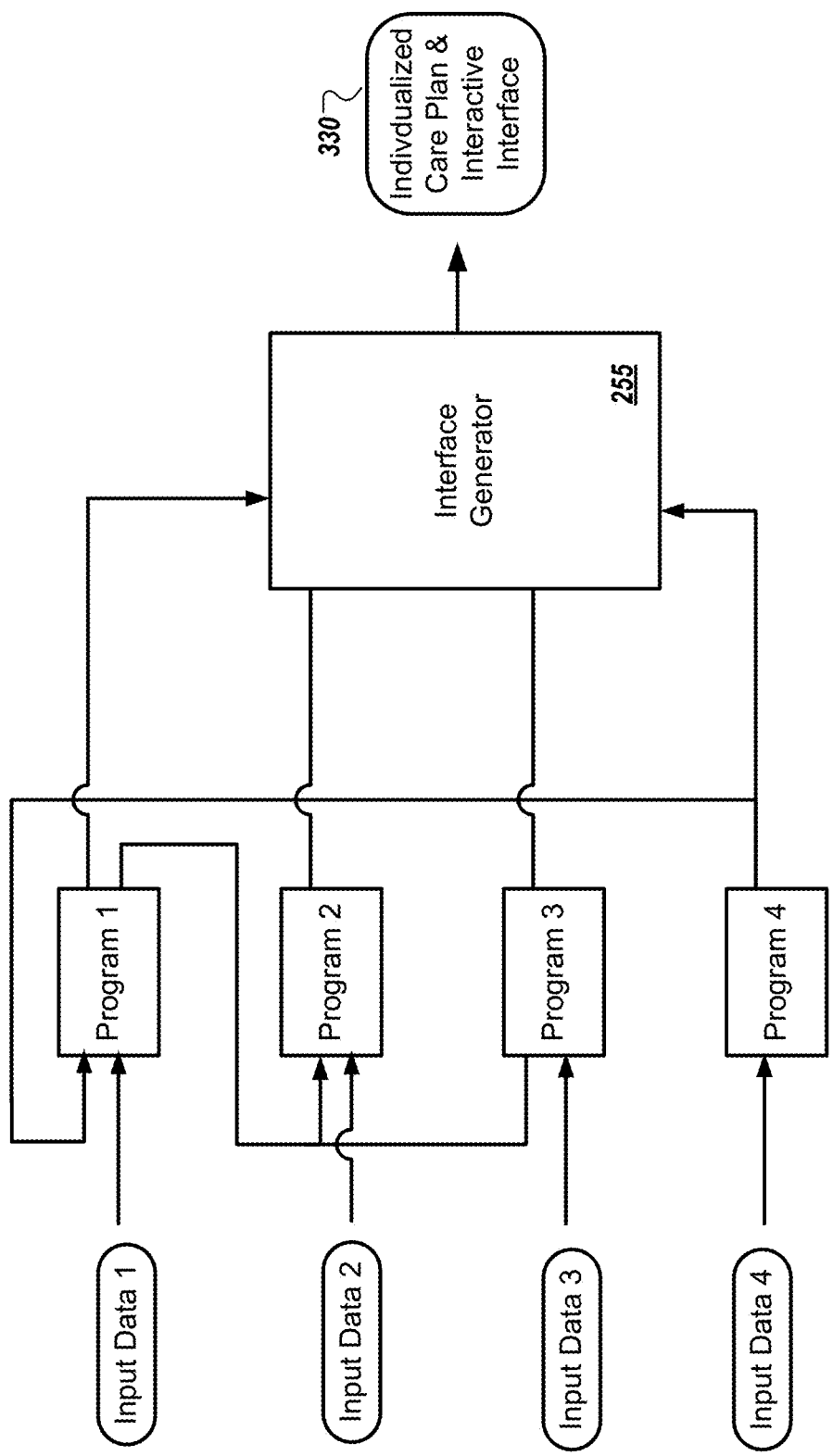

FIGS. 4A-4B are diagrams that illustrate examples of techniques for adjust states of digital therapeutics programs.

FIG. 4A shows an arrangement 400 of elements in which each of various programs 240a-240d receive an input data set used to evaluate their corresponding rules. These data sets may be the same for each program or different for different programs. In addition to receiving the input data representing a user's current status and historical information, each program receives a signal from the program state setting module 253. The module 253 assesses input data 310 which may include any or all of the information used by the programs 240a-240d. The module 253 issues program state instructions which can dynamically change the level or state of each program as the module 253 determines appropriate.

As the programs provide output to the interface generator 255, the output of the programs is also provided to the program state setting module 253. The output can represent messages to be provided to a user, questions to be asked in a survey, interactive activities of the application, indications of media provided to the user, and so on. The module 253 may analyze these program outputs and use the analysis results to change the current levels of the programs. The program state setting module 253 can analyze the outputs of the various programs in a number of ways. For example, the module 253 may extract text from questions or messages initiated by the programs, and map keywords and phrases in the extracted text to different topics. Other mappings may indicate relationships between topics and programs, allowing output of one programs to be assessed for relevance to other programs. Sentiment analysis can also be performed on the outputs of the programs, allowing the module 253 to determine, for example, whether symptoms or other items mentioned are improving or worsening. The module 253 may also assess the frequency of activity of each program, for example, determining whether a program is initiating communication with increasing or decreasing frequency, and take this into account in assessing which programs and levels are likely to be needed.

The module 253 also receives data indicating the current level and segment that is active for each program, and this data also is used by the module 253 to update the levels of the programs. As shown in FIG. 4A, the program state setting module 253 may use information from any or all of the programs to set the state of any or all of the other programs. From data indicating the progress of various users over the course of using a care plan, the program state setting module may infer which combinations of program, program levels, and even specific segments of programs are most effective at assisting users. This analysis may be done across a variety of dimensions. For example, different groups may be assessed by symptoms experienced, intensity of symptoms, type of cancer experienced, stage of cancer or length of time in remission, types of treatments used, types of medications currently administered or previously administered, age, location, nutrition choices, physical activity levels, and many other factors.

For example, the server system 110 may determine that for a breast cancer survivor currently experiencing fatigue one year into remission, a certain set of programs and levels provides a high likelihood of reducing the fatigue. Similarly, the analysis may show that a different set of programs is determined to be effective for a patient currently being treated with radiation for prostate cancer who has historically had high activity levels but recently has reduced his exercise levels.

For each of the various permutations of symptom combinations, cancer types, and other factors, the server system 110 may identify examples from its data set that represent the same or similar combination of aspects. Then, with information about how users have progressed with different combinations of programs and levels active, the server system 110 can assign likelihood scores indicating, for example, a probability that each level of each program is to achieve a desired result, such as reduction of a symptom or other outcome. The same analysis may be done to determine scores for different combinations of programs and levels. These likelihood scores may be used directly by the program state setting module 253. As another example, the likelihood scores may be assessed by the server system 110 to define rules that the program state setting module 253 applies to automatically initiate changes in program states.

In some implementations, the server system 110 may determine the specific set of factors experienced by an individual at a given time, and identify examples of users having the same or similar factors, based on databases of information maintained by the server system 110. The server system 110 may thus define, at various times, custom data sets from historical information about other users to determine a user specific likelihood of desired outcomes for the user's current situation. These user-specific measures may be used by the program state setting module 253, along with user-specific risk levels discussed above, to adjust program states.

FIG. 4B shows another example of automatic transitions between program states. By contrast with FIG. 4A, a predetermined set of connections is used between the programs. For example, program 1 has its state adjusted based on the output or state of program 4, but the decision does not take into account the output of or state of program 2 and program 3.

In addition, rather than including a centralized program state setting module 253, the rules of each program set the state of the program or another program. For example, program 4 may include rules that adjust the level of program for based on the input data to the program, which may indicate historical information about the user. Program 4 may also provide a signal to program 1 indicating that a level of program 1 should be changed. Alternatively, the level of program 4, or outputs to be provided to the user from program 4, maybe provided as input to program 1 and used to adjust program 1 according to program 1's own rules.

Figure 5:
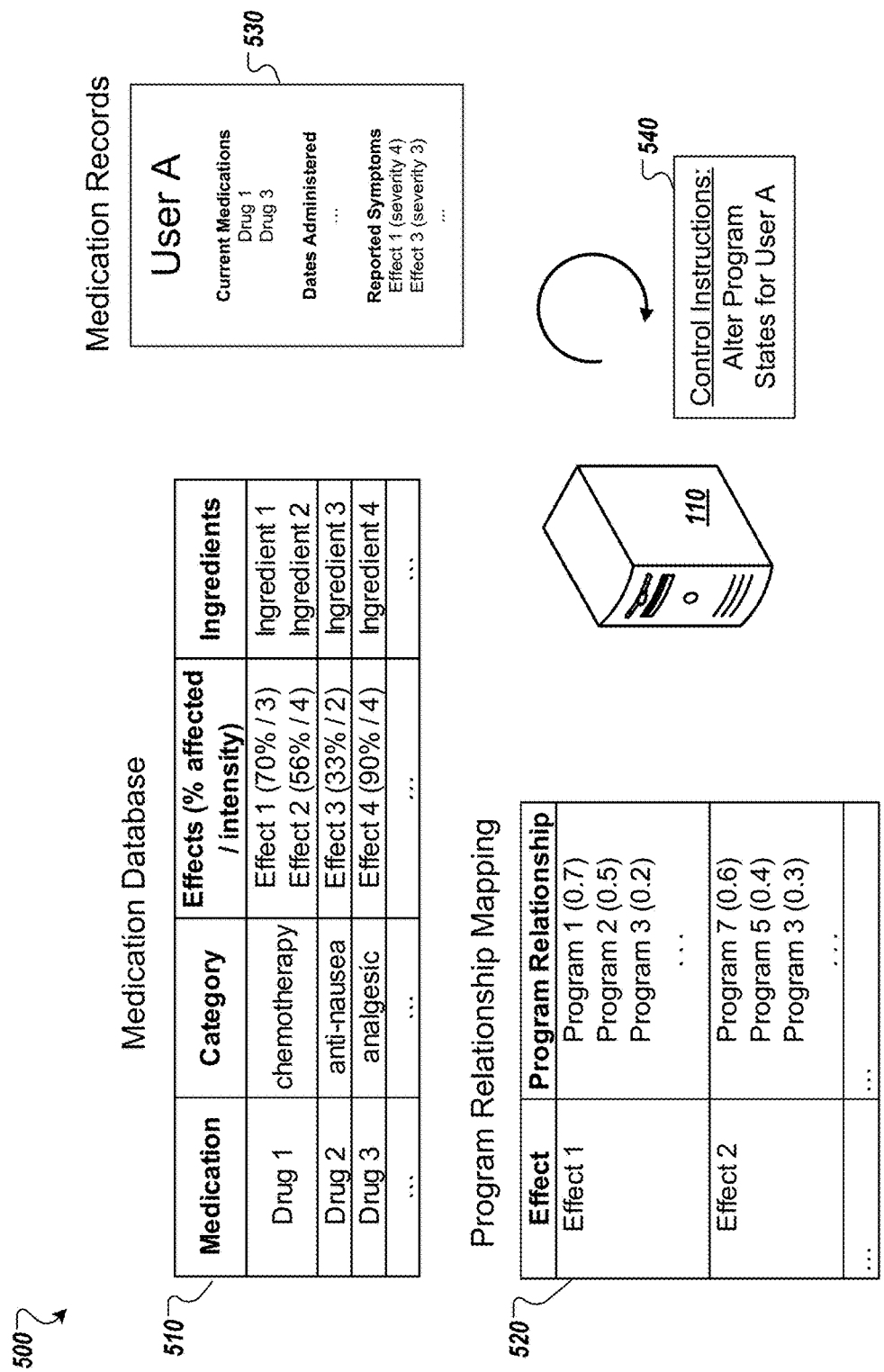
FIG. 5 is a diagram that illustrates examples of using medication information.

FIG. 5 is a diagram that illustrates examples of using medication information. The server system 110 can store information about various pharmaceuticals, as illustrated by medication database 510. As examples, medications can be indicated by an identifier and other information such as a name, category or type, manufacturer, manufacturing lot, etc. For each medication, effects of the medication (potentially both desired and undesired effects) can be specified as well as a list of ingredients, relative or absolute measures of amounts of the ingredients, and other information. The information about effects of the medications can indicate various scores, such as a likelihood score that a person taking the medication will experience the effect or a percentage indicating what percentage of people taking the medication experience the effect. Scores indicating the severity of the effect, e.g., an average measure for those who do experience the effect, can also be indicated The server system 110 can also store a mapping 520 indicating relationships between the effects of medications and different programs. For example, for a given medication effect, scores may be provided indicating a degree of relevance to different programs. The score may represent a relevance of the program or a degree to which the program can address the effect. For example, if the medication effect is insomnia, a sleep disorder program may have a high score in the mapping, since it includes content and interventions that can reduce the effect of that symptom. Similarly, a program for physical exercise or anxiety may have a score in the mapping that indicates a moderate relevance, since those programs may help also but to a lesser degree. The scores in the mapping 520 do not need to be based on intuitive relationships, however, and may be determined through analysis of clinical data tracked over time or through historical outcomes of users of the system. The scores may be manually defined in some instances.

The server system 110 also stores medication records 530 for each user. These records 530 can indicate current medications of the user as well as historical information about medications of the user. The records 530 can indicate a variety of metadata or contextual information about how and when the medications were administered, such as dates, times, doses, whether taken with food, form (e.g., patch, pill, injection, etc.), indication of prescribed usage (e.g., allowing the system to determine whether actual use corresponds with prescribed use), and so on. In addition, actual symptoms, side effects, or beneficial effects that the user experienced can be specified, as reported by the user directly through a mobile device, or through medical records or doctors assessments.

From the medication records 530 and other user data, the server system 110 can learn the appropriate mappings 520 and effects of medications. For example, with the data collected and assessed by the server system 110, previously unknown side effects or benefits of certain medications or combinations of medications can be discovered. Similarly, long-term effects of medications can be more accurately characterized and predicted. For example, the chemotherapy medications that a user took a year or two ago may contribute to ongoing or even later-arising symptoms. Even before these relationships are widely known or clinically proven, the server system 110 can identify these effects and characterize them in the medication database 510, e.g., with risk levels, typical severity, and factors contributing to increased risk. The mappings 520 can then indicate, for those effects, which program or combinations of programs are most effective in assisting a user to deal with the effects.

Using the user's medication records 530, and the indications of which medications were taken when, the server system 110 can look up in the medication database 510 which medication effects are likely for the user. In addition, the server system 110 can use the mapping 520 to determine which programs (and potentially specific levels and segments of the programs) are most relevant to the likely effects. Given a likely effect predicted using the medication records, or from actual effects indicated by the medication records, the server system 110 identifies the relevance scores for one or more programs. The server system 110 may then combine the scores across different effects.

For example, all effects of current medications of a user and former medications of a user can be determined. The scores in the mapping 520 are determined for each of these effects. Then, for each program, the relevance scores may be combined by weighting the values. Scores corresponding to likely effects may be weighted or discounted according to the likelihood from the medication database 510. Similarly, scores for effects estimated from medications that are not current may be discounted in some instances based on how long ago the corresponding medication was administered. Similarly, scores can be weighted by the typical intensity of the effect. By contrast, for actual effects experienced by the user, the scores from the mapping 520 may not be discounted, or may be increased. The weighted scores for a program may then be added or otherwise combined to give an overall measure of the likely relevance of the program to the user given the user's current medications and medication history. The combined scores for the program are then compared to a threshold, and if the score satisfies the threshold, the corresponding program may be activated or have its level increased. The same technique can be used for each of the programs available.

With these techniques, the system 110 can activate digital therapeutics programs to address the actual effects experienced by a patient. The system 110 can also activate programs to address potential effects that may be likely but may not be reported by a patient or may be developed in the future. The server system 110 can generate control instructions 540 that specify specific programs to activate, deactivate, or change in level based on the analysis of the user's medication records 530, and based on the other information discussed above.

In some implementations, the records can include pharmacogenomics data from individual users. This information can allow cancer medications and related medications to be cross-referenced with the patient's genetic data. The server system 110 can use this information to estimate how medications have affected or will affect a user. For example, the server system 110 can perform an analysis of a patient's genetic profile to identify genes that affect the metabolism of specific medications. For example, there one set of genes may regulate medication metabolism in the liver, and variations in those genes may result in different metabolism rates for different individuals. Having identified genes that affect how a medication is processed by a user, the server system 110 can use the information to predict which medications may have adverse effects, may have stronger or weaker effects than expected, and so on. These results can be provided as a notice or warning to a user, family member or friend, caregiver or other health service provider, pharmacist, or other person. Similarly, the information can be provided to the digital therapeutics programs to provide current interventions. For example, if a user's genetic profile indicates genes that would cause a currently prescribed drug to metabolize in a manner that causes increased drowsiness, the corresponding scores for that side effect can be increased (with respect to probability and/or severity) for that particular user. Similarly, since the increased side effect risk may be a discouragement to actually taking the medication, the system 110 may determine that an additional level increase for a medication compliance program is appropriate, or that a caregiver should be notified to be more specifically verify that the medication is properly taken.

In some implementations, user pharmacogenomics data can also be used to identify or verify relationships between specific genetic features and effects of medications. For example, given the self-reported assessment results for pain, mood, and other characteristics, as well as activity levels detected with sensor data and confirming messages from caregivers and friends and family, the system 110 can identify correlations among specific genetic features, or combinations of genetic features, and certain effects of medications. This information may be used to update the medication database to provide scores for effect probability and intensity that are more specific for people with certain genetic profiles than for the population as a whole. As a result, in some implementations, the relationships between genetic features of individuals and likely effects of medication need not be predetermined, and can be learned and adjusted dynamically by the system over time through the analysis of changes in user survey results and monitored actions.

Figure 6:
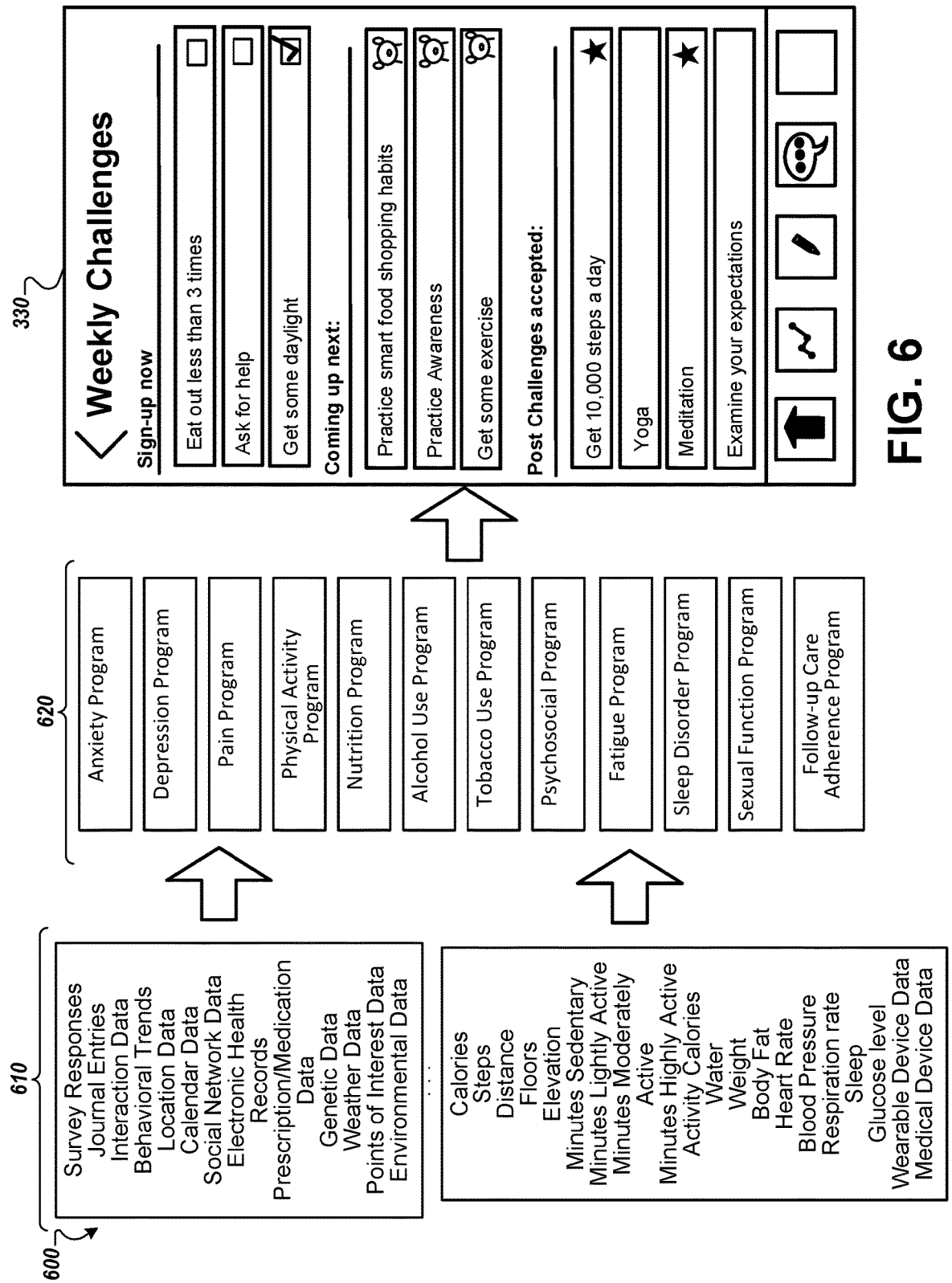
FIG. 6 is a diagram that illustrates examples of data that can be used by various digital therapeutics programs.

FIG. 6 illustrates additional examples of data that can be used by various digital therapeutics programs.

As illustrated, the server system 110 may receive various types of input data 610 such as survey responses, journal entries, interaction data, behavioral trends, location data, calendar data, social network data, electronic health records, prescription/medication data, genetic data, and other information about a user. Other input data 610 may represent general information, which may not be specific to a user can include weather data, points of interest data, environmental data, and so on. The types of data about a user that may be tracked include calories consumed, steps taken, distance walked, floors walked, elevation, minutes sedentary, minutes lightly active, minutes moderately active, minutes highly active, calories used during physical activity, water consumption, weight, body fat, heart rate, blood pressure, respiration rate, sleep times and amounts, glucose levels, wearable device data, medical device data, and so on.

A number of digital therapeutics programs 620 are shown as examples. These programs may each have their own sets of content and rules that govern how they interact with users. Each program may be activated and deactivated separately to support a different aspect of a user's wellbeing. Nevertheless, as discussed above, the levels or states of the programs may be adjusted based on the outputs and states of other programs to respond to a user's situation and to proactively provide support for expected challenges. In the illustration, separate programs are shown for anxiety, depression, pain, physical activity, nutrition, alcohol use, tobacco use, psychosocial needs, fatigue, sleep disorders, sexual function, and adherence to follow-up care. Each of these programs may use any and all of the inputs to the server system 110 to determine how to interact with a user. The specific subset of programs that is active in a user's care plan at a given time, with the active segments and levels of those programs, is used to process the input data 610 and provide an individualized care plan and interactive user interfaces 330.

While the techniques discussed herein are well-suited to serving cancer patients and cancer survivors, the same techniques can also be applied to provide digital therapeutics and improve wellness in other people also. For example, people who have a chronic physical condition, such as arthritis, diabetes, hepatitis, heart disease, COPD, etc., can also benefit from the application of various digital therapeutics programs and the analysis and adjustment in programs that the system provides. Similarly, the system may be used to treat and support users with psychological conditions such as depression, anxiety disorder, attention-deficit/hyperactivity disorder, bipolar disorder, etc. To assists these users, and any of the other types of users, the system may use cognitive behavioral therapy techniques to assist the users in adjusting behaviors, mood, etc. As another example, the system can be used to treat and support users recovering from a discrete event, such as surgery or trauma, e.g., a broken bone, a joint replacement, cataract surgery, and so on. As another example, the system may be used to support users in achieving general health, e.g., physical and/or psychological wellbeing. The system can encourage and guide users to improve or maintain a lifestyle on a day-to-day, or even moment-to-moment basis, as the various digital therapeutics programs determine are appropriate for the user given the current situation. As an example, programs for nutrition and physical fitness can prompt users to take incremental steps to reach goals that are set by the user or by the system. For all of these potential uses of the system and the different types of users, the ability for various digital therapeutics programs to interact and dynamically set their can provide improved responsiveness and efficiency of the system.

Accordingly, in some implementations, the system can be used with different types of users who are not cancer patients or cancer survivors.

As discussed above, the states of different programs can be dynamically adjusted, based on current information about a user, historical information about the user, and based on the states of other programs. In addition, the types of interconnections between programs, e.g., the rules that define transitions between program states can also dynamically updated based on various factors. For example, the system can use information about the progress and symptoms of users over time can be used to identify conditions or triggers that should cause state transitions. Groups of users that have certain commonalities can be identified and their progress assessed to determine these conditions and triggers, and which actions to perform, e.g., which programs to activate or deactivate, and which levels are most effective. In addition to or instead of using data about users of the system, population-level data can be used in a similar manner to determine which combinations of programs and interventions are appropriate for different users. The population-level data may represent information about a population of a city, county, state or province, country, continent, or the world. Combining information from the data sets of users of the system with population-level data can provide increased accuracy of predictions, better enabling the system to identify predicted interactions and interventions that will address the patient's current or expected needs.

Embodiments of the invention and all of the functional operations described in this specification may be implemented in digital electronic circuitry, or in computer software, firmware, or hardware, including the structures disclosed in this specification and their structural equivalents, or in combinations of one or more of them. Embodiments of the invention may be implemented as one or more computer program products, i.e., one or more modules of computer program instructions encoded on a computer-readable medium for execution by, or to control the operation of, data processing apparatus. The computer readable medium may be a non-transitory computer readable storage medium, a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, embodiments of the invention may be implemented on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

Embodiments of the invention may be implemented in a computing system that includes a back end component, e.g., as a data server, or that includes a middleware component, e.g., an application server, or that includes a front end component, e.g., a client computer having a graphical user interface or a Web browser through which a user may interact with an implementation of the invention, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

In each instance where an HTML file is mentioned, other file types or formats may be substituted. For instance, an HTML file may be replaced by an XML, JSON, plain text, or other types of files. Moreover, where a table or hash table is mentioned, other data structures (such as spreadsheets, relational databases, or structured files) may be used.

Thus, particular embodiments of the invention have been described. Other embodiments are within the scope of the following claims. For example, the actions recited in the claims may be performed in a different order and still achieve desirable results.

What is claimed is:

1. A system comprising:
   a server system configured to provide digital therapeutics administered through individualized application content determined based on interaction with a plurality of networked devices, wherein the server system is configured to generate the individualized application content using different combinations of programs from a plurality of digital therapeutics programs that each correspond to a different aspect of cancer treatment and cancer survivorship, each of the digital therapeutics programs having multiple predetermined program states, at least some of the different program states each specifying different levels of interaction or different levels of intensity of the corresponding digital therapeutics program when the digital therapeutics program is active for a user, each of the different program states having a different corresponding set of rules that control interaction of the digital therapeutics program with a user;

wherein the server system is configured to communicate with a first device, a second device, and a third device over a network to provide digital therapeutics interventions to a first user that is a cancer patient or a cancer survivor, wherein:

the first device has an interactive application configured to provide digital therapeutics for a cancer patient or cancer survivor in cooperation with the server system, the first device being associated with the first user;

the second device has an interactive application that is configured to initiate interactions with a user of the second device based on communications from the server system, wherein the user of the second device is a caregiver for the first user; and the third device has an interactive application that is configured to initiate interactions with a user of the third device based on communications from the server system, wherein the user of the third device is a friend of family member of the first user; and wherein the server system comprises one or more computers and one or more storage devices storing executable instructions that, when executed by the one or more computers, cause the server system to perform operations comprising:

communicating individualized application content to the first device, the second device, and the third device, wherein the server system generates the individualized application content using the plurality of digital therapeutics programs that each correspond to a different aspect of cancer treatment and cancer survivorship, the server system being configured to generate the individualized application content using combinations of the digital therapeutics programs and user-specific sets of program states of the digital therapeutics programs for the first user;

automatically varying, by the server system, treatment of the first user by altering the user-specific set of program states of the plurality of digital therapeutics programs to assign an updated user-specific set of program states for the first user, wherein the server system enforces interdependence of the digital therapeutics programs by altering the program states for the first user for at least some of the digital therapeutics programs based on stored data indicating the program states of one or more of the other digital therapeutics programs for the first user;

generating, by the server system and for each of the plurality of digital therapeutics programs, second individualized application content for the first user by applying, for each of the active digital therapeutics programs, the set of rules corresponding to the updated program state for the digital therapeutics program;

distributing, by the server system and to the first device, the second individualized application content generated for the first user according to the updated user-specific set of program states for the first user; and providing, by the server system, data to the second device and the third device that is generated based on the updated user-specific set of program states for the first user, wherein the provided data alters interactions of the interactive applications of the second device and the third device with their respective users.

2. The system of claim 1, wherein varying the user-specific set of program states comprises:

automatically enabling one or more digital therapeutics programs for the first user such that the server system initiates use of the enabled program to generate individualized application content for the first user; or automatically disabling one or more digital therapeutics programs for the first user such that the server system discontinues use of the enabled program to generate individualized application content for the first user.

3. The system of claim 1, wherein at least some of the program states correspond to different time periods representing sequential progression through a predetermined elements of the digital therapeutics programs.

4. The system of claim 1, further comprising:

determining, according to one or more of the digital therapeutics programs that are currently active for the first user, an attribute of the first user to be obtained; and providing, to second device or the third device, data for an interactive interface for acquiring information indicative of the attribute of the first user;

wherein distributing the first individualized application content comprises distributing individualized application content for the first user that is based on input from the second device or the third device.

5. The system of claim 1, wherein automatically varying the program states comprises automatically varying the program states according to sensor data generated by the first device, status information generated by computer systems of medical practitioners, and results of adaptive interactive forms customized for the first user.

6. The system of claim 1, wherein automatically varying the program states comprises automatically varying the program states according to:

(i) at least one general data source providing one or more of weather data, points of interest data, or environmental data; and (ii) at least one user-specific data source comprising data from:
a wireless wearable device of the first user,
a wirelessly connected medical device of the first user,
electronic health records for the first user,
prescription data for the first user,
genetic data for the first user,
social media data for the first user, or
mobile device data from a mobile device of the first user.

7. The system of claim 1, wherein the server system is configured to automatically vary the program states based on behavioral patterns of multiple cancer patients or cancer survivors, as identified by the server system based at least in part on sensor data acquired by client devices of the multiple cancer patients or cancer survivors.

8. The system of claim 1, wherein the operations further comprise:

based on identifying a particular combination of digital therapeutics program states corresponding to a specific health outcome, defining, by the server system, a digital biomarker for the specific health outcome as the particular combination of digital therapeutic programs being concurrently active with particular program states set for the active programs;

identifying, by the server system and based on program state transitions of users that have previously exhibited the digital biomarker, combinations of digital therapeutics program states applied for the users that reduced symptoms of the users over the course of the program state transitions; and determining, by the server system, that the first user exhibits the digital biomarker based on the user-specific set of program states for the first user indicating that the particular combination of digital therapeutic programs is currently active with the particular program states for the active programs;

wherein altering the user-specific set of program states of the plurality of digital therapeutics programs comprises assigning, by the server system and in response to determining that the first user exhibits the digital biomarker, updated user-specific set of program states for the first user to include one or more program states identified as reducing symptoms of the users identified as having the digital biomarker.

9. A method comprising:

communicating, by server system, individualized application content over a network to (i) a first device associated with a first user that is a cancer patient or cancer survivor, (ii) a second device associated with a caregiver of the first user, and (iii) a third device associated with a friend or family member of the first user, wherein the server system generates the individualized application content using a plurality of digital therapeutics programs that each correspond to a different aspect of cancer treatment and cancer survivorship, wherein each of the digital therapeutics programs have multiple predetermined program states, at least some of the different program states each specifying different levels of interaction or different levels of intensity of the corresponding digital therapeutics program when the digital therapeutics program is active for a user, each of the different program states having a different corresponding set of rules that control interaction of the digital therapeutics program with a user, and wherein the server system is configured to generate the individualized application content using combinations of the digital therapeutics programs and user-specific sets of program states of the digital therapeutics programs for the first user;

automatically varying, by the server system, treatment of the first user by altering the user-specific set of program states of the plurality of digital therapeutics programs to assign an updated user-specific set of program states for the first user, wherein the server system enforces interdependence of the digital therapeutics programs by altering the program states for the first user for at least some of the digital therapeutics programs based on stored data indicating the program states of one or more of the other digital therapeutics programs for the first user;

generating, by the server system and for each of the plurality of digital therapeutics programs, second individualized application content for the first user by applying, for each of the active digital therapeutics programs, the set of rules corresponding to the updated program state for the digital therapeutics program;

distributing, by the server system and to the first device, the second individualized application content generated for the first user according to the updated user-specific set of program states for the first user; and providing, by the server system, data to the second device and the third device that is generated based on the updated user-specific set of program states for the first user, wherein the provided data alters interactions of the second device and the third device with their respective users.

10. The method of claim 9, wherein varying the user-specific set of program states comprises:

automatically enabling one or more digital therapeutics programs for the first user such that the server system initiates use of the enabled program to generate individualized application content for the first user; or automatically disabling one or more digital therapeutics programs for the first user such that the server system discontinues use of the enabled program to generate individualized application content for the first user.

11. The method of claim 9, wherein the program states correspond to different time periods representing sequential progression through a predetermined elements of the digital therapeutics programs.

12. The method of claim 9, wherein automatically varying the program states comprises automatically varying the program states according to sensor data generated by the first device, status information generated by computer systems of medical practitioners, and results of adaptive interactive forms customized for the first user.

13. The method of claim 9, wherein automatically varying the program states comprises automatically varying the program states according to:

(i) at least one general data source providing one or more of weather data, points of interest data, or environmental data; and (ii) at least one user-specific data source comprising data from:
 a wireless wearable device of the first user,
 a wirelessly connected medical device of the first user,
 electronic health records for the first user,
 prescription data for the first user,
 genetic data for the first user,
 social media data for the first user, or
 mobile device data from a mobile device of the first user.

14. The method of claim 9, further comprising setting and storing, for the first user, user-specific target levels for measures corresponding to the digital therapeutics programs;

wherein automatically varying the program states comprises:
 identifying trends in the measures for the first user; and
 varying the program states based in part on the identified trends and the user-specific target levels for the first user.

15. The method of claim 9, further comprising:

storing, by the server system, program status data indicating a set of multiple of the digital therapeutics programs that are active for the first user a particular time, the program status data also indicating a program state for each of the multiple digital therapeutics programs that are active at the particular time, the program state for each digital therapeutics program being selected from among the program states of the digital therapeutics program;

identifying, by the server system, a particular combination of digital therapeutics program states corresponding to a specific health outcome based on a determination that patients experiencing the particular combination of digital therapeutics program states are likely to experience the specific health outcome; and based on identifying the particular combination of digital therapeutics program states corresponding to a specific health outcome, defining, by the server system, a digital biomarker for the specific health outcome as the particular combination of digital therapeutic programs being concurrently active with particular program states set for the active programs.

16. The method of claim 15, further comprising:
identifying, by the server system, a group of users that have previously exhibited the digital biomarker by having the particular combination of digital therapeutic programs being concurrently active with the particular program states set for the active programs;
determining, by the server system, subsequent program state transitions of the users in the group after exhibiting the digital biomarker, wherein the program state transitions of the users are made based on a combination of factors including a user's personal goals, measured health status, tracked behavior patterns, sensor data from one or more mobile devices, and user interactions with a computing device; and
identifying, by the server system and based on the program state transitions of the users in the group, combinations of digital therapeutics program states applied for the users in the group that reduced symptoms of the users over the course of the program state transitions.

17. The method of claim 16, further comprising determining, by the server system, that the first user exhibits the digital biomarker based on the user-specific set of program states for the first user indicating that the particular combination of digital therapeutic programs is currently active with the particular program states for the active programs;
wherein altering the user-specific set of program states of the plurality of digital therapeutics programs comprises assigning, by the server system, updated user-specific set of program states for the first user in response to determining that the first user exhibits the digital biomarker and based on the program state transitions made for the users in the group after the users in the group exhibiting the digital biomarker; and
wherein the updated user-specific set of program states for the first user are updated to include one or more program states selected from the combinations of digital therapeutics program states identified as reducing symptoms of the users identified as having the digital biomarker.

18. The method of claim 17, wherein the second individualized application content causes the first device to record a measurement from one or more devices in communication with the first device.

19. One or more non-transitory computer-readable media storing instructions that, when executed by one or more computers of a server system, cause the one or more computers to perform operations comprising:

communicating, by server system, individualized application content over a network to (i) a first device associated with a first user that is a cancer patient or cancer survivor, (ii) a second device associated with a caregiver of the first user, and (iii) a third device associated with a friend or family member of the first user,
wherein the server system generates the individualized application content using a plurality of digital therapeutics programs that each correspond to a different aspect of cancer treatment and cancer survivorship,
wherein each of the digital therapeutics programs have multiple predetermined program states, at least some of the different program states each specifying different levels of interaction or different levels of intensity of the corresponding digital therapeutics program when the digital therapeutics program is active for a user, each of the different program states having a different corresponding set of rules that control interaction of the digital therapeutics program with a user, and
wherein the server system is configured to generate the individualized application content using combinations of the digital therapeutics programs and user-specific sets of program states of the digital therapeutics programs for the first user;
automatically varying, by the server system, treatment of the first user by altering the user-specific set of program states of the plurality of digital therapeutics programs to assign an updated user-specific set of program states for the first user, wherein the server system enforces interdependence of the digital therapeutics programs by altering the program states for the first user for at least some of the digital therapeutics programs based on stored data indicating the program states of one or more of the other digital therapeutics programs for the first user;
generating, by the server system and for each of the plurality of digital therapeutics programs, second individualized application content for the first user by applying, for each of the active digital therapeutics programs, the set of rules corresponding to the updated program state for the digital therapeutics program;
distributing, by the server system and to the first device, the second individualized application content generated for the first user according to the updated user-specific set of program states for the first user; and
providing, by the server system, data to the second device and the third device that is generated based on the updated user-specific set of program states for the first user, wherein the provided data alters interactions of the second device and the third device with their respective users.

* * * * *